(12) United States Patent
Woods, Jr. et al.

(10) Patent No.: US 12,642,645 B2
(45) Date of Patent: Jun. 2, 2026

(54) SURGICALLY IMPLANTED THERAPEUTIC/DIAGNOSTIC OCULAR OPTICAL ARRAY

(71) Applicant: GlaiveRF, Inc., Burlington, MA (US)

(72) Inventors: Wayne H. Woods, Jr., Carlisle, MA (US); Christopher Shelby, Shreveport, LA (US)

(73) Assignee: GLAIVE MEDICAL OPTICS, INC, Chelmsford, MA (US)

( * ) Notice: Subject to any disclaimer, the term of this patent is extended or adjusted under 35 U.S.C. 154(b) by 644 days.

(21) Appl. No.: 18/082,884

(22) Filed: Dec. 16, 2022

(65) Prior Publication Data

US 2023/0194949 A1     Jun. 22, 2023

Related U.S. Application Data

(60) Provisional application No. 63/355,165, filed on Jun. 24, 2022, provisional application No. 63/290,302, filed on Dec. 16, 2021.

(51) Int. Cl.
| | |
|---|---|
| *A61B 3/12* | (2006.01) |
| *A61B 3/024* | (2006.01) |
| *A61B 3/14* | (2006.01) |
| *A61F 2/14* | (2006.01) |
| *G02F 1/29* | (2006.01) |

(52) U.S. Cl.
CPC ................ *A61F 2/14* (2013.01); *A61B 3/024* (2013.01); *A61B 3/12* (2013.01); *A61B 3/14* (2013.01); *A61F 2250/0001* (2013.01); *A61F 2250/0002* (2013.01); *G02F 1/292* (2013.01)

(58) Field of Classification Search
CPC ............ A61F 2/1613; A61F 2250/0001; A61F 2250/0002; A61F 2/16; A61F 2/1659; A61F 2002/1681; A61F 2002/169053; A61F 2/1694; A61F 2002/1699; G02F 1/292
See application file for complete search history.

(56) References Cited

U.S. PATENT DOCUMENTS

| | | |
|---|---|---|
| 4,936,850 A | 6/1990 | Barrett |
| 6,874,888 B1 | 4/2005 | Dudai |
| (Continued) | | |

OTHER PUBLICATIONS

International Search Report and Written Option of the International Searching Authority from PCT Application No. PCT/US2022/053180 dated Apr. 5, 2023, 8 pages.
(Continued)

*Primary Examiner* — Sarah W Aleman
*Assistant Examiner* — Paris Marie Blass
(74) *Attorney, Agent, or Firm* — Andrew D. Wright; Calderon Safran & Wright P.C.

(57) ABSTRACT

A surgically implanted ocular optical array that can be used in both therapeutic and diagnostic applications is described. A device configured to be implanted in an eye includes: an imaging system that receives visible light incoming to the eye; optical source generating circuitry that generates an optical signal based on the light received by the imaging system; and an optical phased array (OPA) that generates and projects an image onto a retina of the eye in which the device is implanted, the image being based on the optical signal generated by the optical source generating circuitry.

20 Claims, 18 Drawing Sheets

(56) References Cited

U.S. PATENT DOCUMENTS

| | | | |
|---|---|---|---|
| 7,248,928 B2 * | 7/2007 | Yagi | A61F 2/141 |
| | | | 607/139 |
| 7,736,390 B2 | 6/2010 | Aharoni et al. | |
| 8,908,277 B2 | 12/2014 | Pesach et al. | |
| 8,956,396 B1 * | 2/2015 | Friend | A61N 5/0622 |
| | | | 607/88 |
| 8,988,754 B2 | 3/2015 | Sun et al. | |
| 10,944,290 B2 | 3/2021 | Mirjalili et al. | |
| 11,143,885 B2 | 10/2021 | Jow et al. | |
| 2004/0236421 A1 | 11/2004 | Lipshitz et al. | |
| 2008/0008206 A1 | 1/2008 | Cho et al. | |
| 2008/0086206 A1 | 4/2008 | Nasiatka et al. | |
| 2012/0330415 A1 | 12/2012 | Callahan et al. | |
| 2013/0165764 A1 | 6/2013 | Scheuermann et al. | |
| 2014/0058294 A1 | 2/2014 | Gross et al. | |
| 2014/0228715 A1 | 8/2014 | Schroeder et al. | |
| 2014/0266953 A1 | 9/2014 | Yen | |
| 2014/0371227 A1 | 12/2014 | Aube et al. | |
| 2015/0018807 A1 | 1/2015 | Kircher et al. | |
| 2017/0003507 A1 | 1/2017 | Raval et al. | |
| 2017/0023793 A1 | 1/2017 | Shtukater | |
| 2017/0323615 A1 | 11/2017 | Hazra et al. | |
| 2017/0336641 A1 | 11/2017 | von und zu Liechtenstein | |
| 2017/0371227 A1 | 12/2017 | Skirlo et al. | |
| 2019/0065970 A1 * | 2/2019 | Bonutti | G16H 20/10 |
| 2020/0345554 A1 | 11/2020 | Saini | |
| 2020/0355983 A1 | 11/2020 | Lipson et al. | |
| 2020/0409458 A1 * | 12/2020 | Smithwick | A61B 3/103 |
| 2021/0072821 A1 * | 3/2021 | von und zu Liechtenstein | |
| | | | G02C 7/086 |
| 2021/0085449 A1 | 3/2021 | Scharioth et al. | |
| 2021/0290367 A1 | 9/2021 | Wiemer et al. | |
| 2022/0233357 A1 * | 7/2022 | Saini | A61F 2/1624 |
| 2022/0252849 A1 | 8/2022 | Lee | |
| 2022/0257972 A1 | 8/2022 | Kubota et al. | |
| 2024/0138673 A1 | 5/2024 | Woods, Jr. | |
| 2025/0099299 A1 | 3/2025 | Woods, Jr. | |

OTHER PUBLICATIONS

Mills et al., "Electronic Retinal Implants and Artificial Vision: Journey and Present", https://www.ncbi.nlm.nih.gov/omc/articles/PMC5639190/pdf/eye201765a.pdf, Macmillan Publishers Limited, part of Springer Nature, 2017, 16 pages.

Shim et al., "Feasibility of Intraocular Projection for Treatment of Intractable Corneal Opacity", Cornea, DOI: 10.1097/ICO.0000000000001852, vol. 38, No. 4, Apr. 2019, 5 pages.

Rountree et al., "Prototype Chemical Synapse Chip for Spatially Patterned Neurotransmitter Stimulation of the Retina ex vivo", Microsystems & Nanoengineering (2017) 3, 17052; DOI:10.1038/micronano.2017.52, 12 pages.

Haerinia et al., "Wireless Power Transfer Approaches for Medical Implants: A Review", Signals 2020, 1, DOI:10.3390/signals1020012, 21 pages.

Kim et al., "Compact Solid-state Optical Phased Array Beam Scanners Based on Polymeric Photonic Integrated Circuits", www.nature.com/scientificreports, https://www.nature.com/articles/s41598-021-90120-x, 2021, 9 pages.

Anonymous, "Phasedarray optics", https://en.wikipedia.org/wiki/Phased-array_optics, Wikipedia, Archived Dec. 11, 2022, 3 pages.

Kwong et al., "On-chip Silicon Optical Phased Array for Two-dimensional Beam Steering", Abstract, Downloaded Dec. 1, 2022, 1 page.

Lin et al., "High-performance Optical Beam Steering with Nanophotonics", https://www.degruyter.com/document/ doi/10.1515/nanoph-2021-0805/html?lang=en, De Gruyter, Mar. 2, 2022, 47 pages.

Guo et al., "Integrated Optical Phased Arrays for Beam Forming and Steering", Appl. Sci. 11, 4017. https://doi.org/10.3390/app11094017, Apr. 28, 2021, 41 pages.

AAPOS, "Intraocular Lens Implant (IOL)", retrieved from the website https://aapos.org/viewdocument/intraocular-lens-implant-iol on Sep. 25, 2023, 2 Pages.

ASCRS, 2023 ASCRS Annual Meeting On Demand, retrieved from the website https://ascrs.org/clinical-education/presentations-on-demand/meetings/2023-ascrs-annual-meeting?videoid=6327094562112 on Sep. 26, 2023, 6 Pages.

Gortzak, "Development of a Thermomechanically Adjustable IOL", retrieved from the website https://ascrs.org/clinical-education/presentations-on-demand/meetings/2023-ascrs-annual-meeting?videoid=6327094562112 on Sep. 22, 2023, 1 Page.

HighlightOptics, "Standard Microlens Array", retrieved from the website https://www.highlightoptics.com/en/Product/117.html on Dec. 21, 2023, 8 Pages.

Huang et al., "High speed, high power one-dimensional beam steering from a 6-element optical phased array", vol. 20, No. 16, Optics Express 7311, Jul. 16, 2012, 8 pages.

Li Yao, "Intraocular Lens Delivery System" https://liyaovisuals.com/project/intraocular-lens-delivery-system/, Feb. 11, 2019; 2 Pages.

Notaros et al., "Near-Field-Focusing Integrated Optical Phased Arrays", Journal of Lightwave Technology, Digital Object Identifier 10.1109/JLT.2018.2880462, IEEE, 2018, 10 pages.

Tindie, "Wireless charging coil flex antenna with NFC", https://www.tindie.com/products/untemed/wireless-charging-coil-flex-antenna-with-nfc/#product-description, Accessed Sep. 26, 2023; 4 Pages.

PlusUs, "PlusUS Introduces Xpad—The World's Thinnest and First—Ever Flexible Wireless Charging Pad", https:// www.prnewswire.com/news-releases/plusus-introduces-xpad---the-worlds-thinnest-and-first-ever-flexible-wireless-charging-pad-300797555.html Feb. 19, 2019; 5 Pages.

Zeng et al., "All-plasmonic Optical Phased Array Integrated on a Thin-film Platform", www.nature.com/scientificreports, 7:9959, DOI:10.1038/S41598-017-10398-8, Aug. 30, 2017, 10 pages.

Pahlevaninezhad et al., "Nano-optic endoscope for high-resolution optical coherence tomography in vivo", Nat Photonics, 12(9): 540•547, DOI:10.1038/s41566-018-0224-2, Sep. 2018, 18 pages.

Liu et al., "High precision integrated projection imaging optical design based on microlens array", https://opg.optica.org/oe/fulltext.cfm?uri=OE-27-9-12264&id=409092, Apr. 29, 2019; 18 Pages.

Sadeque Reza Khan et al., "Wireless Power Transfer Techniques for Implantable Medical Devices: A Review", Sensors 2020, 20, 3487; DOI:10.3390/s20123487, published Jun. 19, 2020, 58 pages.

Zaleski, "People suffering from macular degeneration, along with other diseases that impair sight, may soon benefit from gene therapy," retrieved from https://www.washingtonpost.com/business/interactive/2024/bionic-eyes-blind-restore-vision/, Apr. 23, 2024, 13 pages.

* cited by examiner

Damaged area of retina 210

Healthy area of retina 215

205

305

310

105

305

310

Retina 510/610/710

Damaged area of retina 515/615/715

805

Healthy area of retina 520/620/720

1102
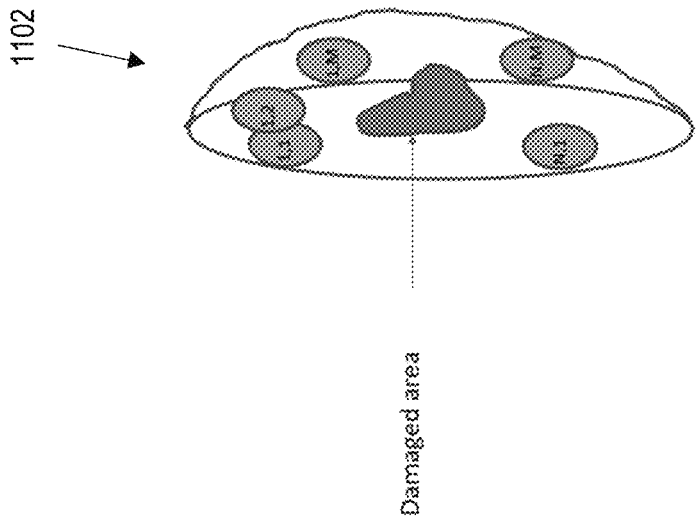
Damaged area
1101
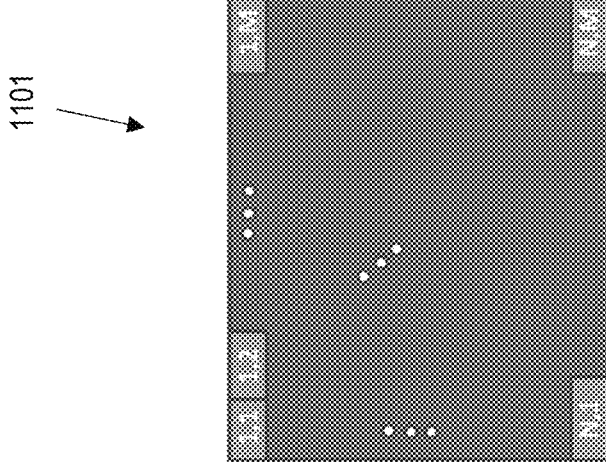
FIG. 11

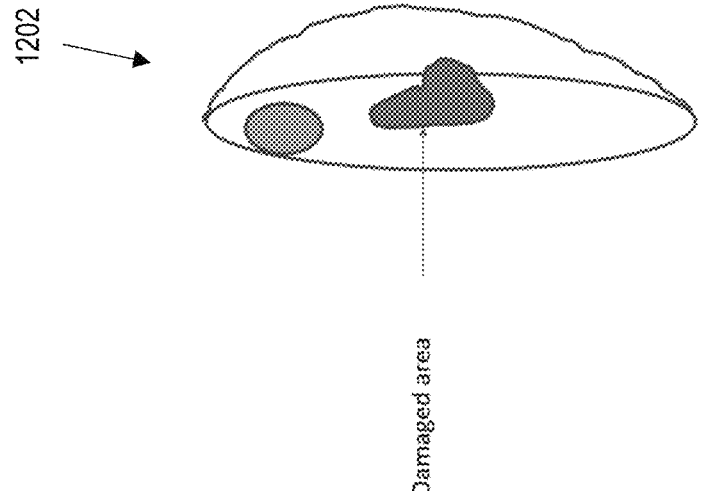
1202
Damaged area
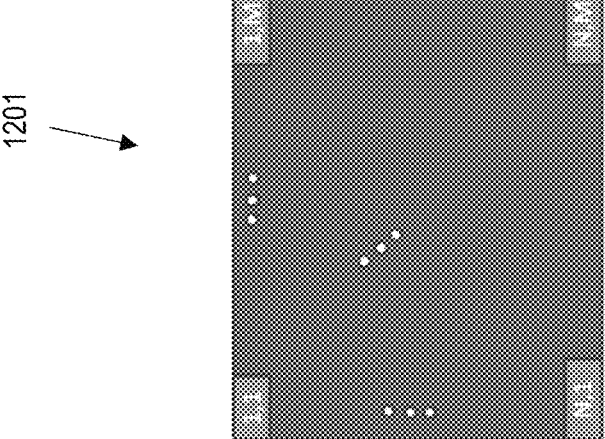
1201
FIG. 12

1301

Diagnostically map retina into functional and non-functional regions using implanted optical array

1302

Intelligent mapping/feedback: could use AI to help determine optimum image-to retina mapping

1303

Program mapping of original image to optical array for correct image formation on healthy retina tissue

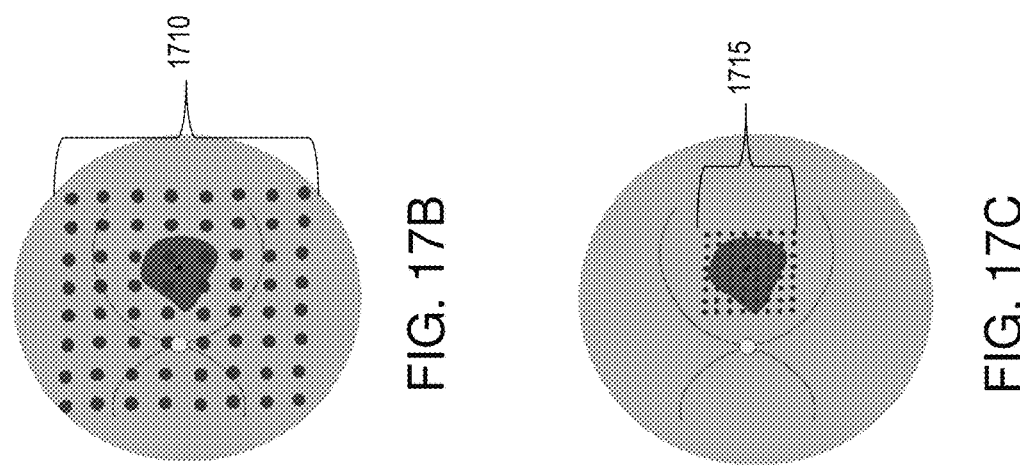

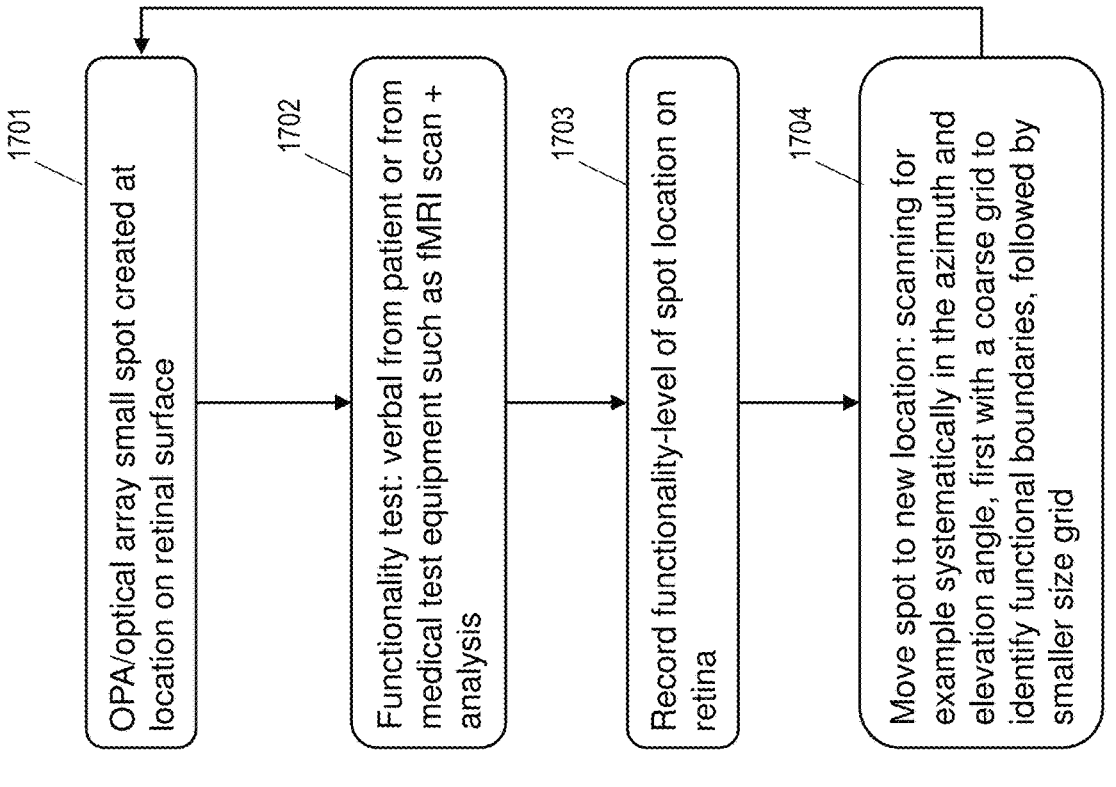

1701

OPA/optical array small spot created at location on retinal surface

1702

Functionality test: verbal from patient or from medical test equipment such as fMRI scan + analysis

1703

Record functionality-level of spot location on retina

1704

Move spot to new location: scanning for example systematically in the azimuth and elevation angle, first with a coarse grid to identify functional boundaries, followed by smaller size grid

FIG. 17A

SURGICALLY IMPLANTED THERAPEUTIC/DIAGNOSTIC OCULAR OPTICAL ARRAY

RELATED APPLICATIONS

This application claims priority to U.S. provisional application No. 63/290,302 filed Dec. 16, 2021, and U.S. provisional application No. 63/355,165 filed Jun. 24, 2022, and both of which are incorporated by reference herein in their entirety.

BACKGROUND

The present invention relates generally to ocular implants and, more particularly, to surgically implanted ocular optical array that can be used in both therapeutic and diagnostic applications.

Being able to target/stimulate specific areas of the retina surface is desirable and difficult to achieve. Approaches to doing this have included chips that directly interface with the neurons in the retina surface. In this disclosure, devices and methods are described that are much less surgically invasive compared to such alternatives.

SUMMARY

In an aspect of the invention, there is a device configured to be implanted in an eye, the device comprising: an imaging system that receives visible light incoming to the eye; optical source generating circuitry that generates an optical signal based on the light received by the imaging system; and an optical phased array (OPA) that generates and projects an image onto a retina of the eye in which the device is implanted, the image being based on the optical signal generated by the optical source generating circuitry.

In an aspect, the device further comprises control circuitry that causes the OPA to project the image onto a determined area of the retina.

In an aspect, the OPA projects the image onto the predetermined area of the retina using beam steering.

In an aspect, the determined area of the retina is a healthy area of the retina.

In an aspect, the control circuitry determines the determined area of the retina using a stored mapping.

In an aspect, the imaging system, the control circuitry, the optical source generating circuitry, and the OPA are arranged in a chip stack.

In an aspect, the imaging system is at a first side of the chip stack, and the OPA is at a second side of the chip stack opposite the first side of the chip stack.

In an aspect, the device comprises a body comprising a central portion and tabs extending outward from the central portion, and the chip stack is in the central portion.

In an aspect, the device further comprises a wireless communication antenna that is configured to receive wireless communication signals from outside the device.

In an aspect, the control circuitry is configured to program the mapping based on the wireless communication signals.

In an aspect, the device further comprises a rechargeable battery that is configured to power the imaging system, the control circuitry, the optical source generating circuitry, and the OPA.

In an aspect, the rechargeable battery is configured to be recharged wirelessly from a charging system located outside the eye.

In an aspect, the device is configured to be implanted in a capsular bag of the eye.

In an aspect, the device is configured to be implanted in a ciliary sulcus of the eye.

In an aspect, the device is configured to be implanted in a chamber of the eye anterior to the iris.

In an aspect, a method includes implanting the device of claim into the eye.

In an aspect, a method includes: causing the device to project a diagnostic image on different locations of the retina of the eye; receiving patient feedback for each of the different locations; creating a mapping of the retina of the eye based on the feedback; and programming the mapping into the device.

In an aspect, the method includes optimizing the mapping using artificial intelligence.

In an aspect, the mapping maps the retina into functional areas and non-functional areas.

In an aspect, the device is configured to control one or more elements of the OPA based on the mapping to project a beam onto a functional area of the retina to reduce or eliminate a scotoma caused by a non-functional area of the retina.

In an embodiment, a device according to any of the aspects above comprises a body made of acrylic and/or silicone lens material.

In an embodiment, a device according to any of the aspects above comprises a single piece lens.

In an embodiment, a device according to any of the aspects above comprises a body having dimensions of 1 mm<=TH<=3 mm and 1 mm<=W<=10 mm.

In an embodiment, in a device according to any of the aspects above comprises, the OPA comprises components of an on-chip optical phase array including but not limited to: one or more splitters, waveguides, phase shifters, amplifiers, and emitting elements.

In an embodiment, a device according to any of the aspects above comprises an imaging chip comprising the imaging system, a control chip comprising the control circuitry, an optical source chip comprising the optical source generating circuitry, and an OPA chip comprising the OPA, wherein the chips are arranged in a chip stack. The chips may be made using semiconductor fabrication materials and techniques, including but not limited to Si, InP, GaAs, Liquid Crystal materials, and BGA/C4/micro-BGA, through substrate (or silicon) vias (TSVs), micro-TSVs, and solder or oxide bonding techniques.

In an embodiment, a device according to any of the aspects above comprises a wireless communication antenna (e.g., for receiving programming signals) and/or an inductive coupling coil (e.g., for wireless charging) embedded in the material of the body.

BRIEF DESCRIPTION OF THE DRAWINGS

The present invention is described in the detailed description which follows, in reference to the noted plurality of drawings by way of non-limiting examples of exemplary embodiments of the present invention.

FIG. 11 shows an exemplary point-to-point pixelated mapping from a 2D directionally programmable optical array to a retina optical nerve surface in accordance with aspects of the invention.

FIG. 12 shows an exemplary point-to-point pixelated mapping from a 2D directionally programmable optical array to a retina optical nerve surface in accordance with aspects of the invention.

FIG. 17A shows a flowchart of an exemplary method in accordance with aspects of the invention.

FIG. 17B shows a coarse grid used in the method of FIG. 17A.

FIG. 17C shows a fine grid used in the method of FIG. 17A.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

The present invention relates generally to ocular implants and, more particularly, to surgically implanted ocular optical array that can be used in both therapeutic and diagnostic applications. In embodiments, a device comprises an optical array, preferably an optical phased array (OPA), integrated to control electronics and charged-coupled device (CCD)/electronic cameras. In embodiments, a camera is integrated in a single assembly with the implanted OPA. In this way, when the device is implanted in an eye of a patient, the patient has vision which tracks with eyeball direction as opposed to, for example, a camera system mounted on a pair of glasses and communicated to the OPA from a wired/tethered or wireless network bridge.

Figure 5:
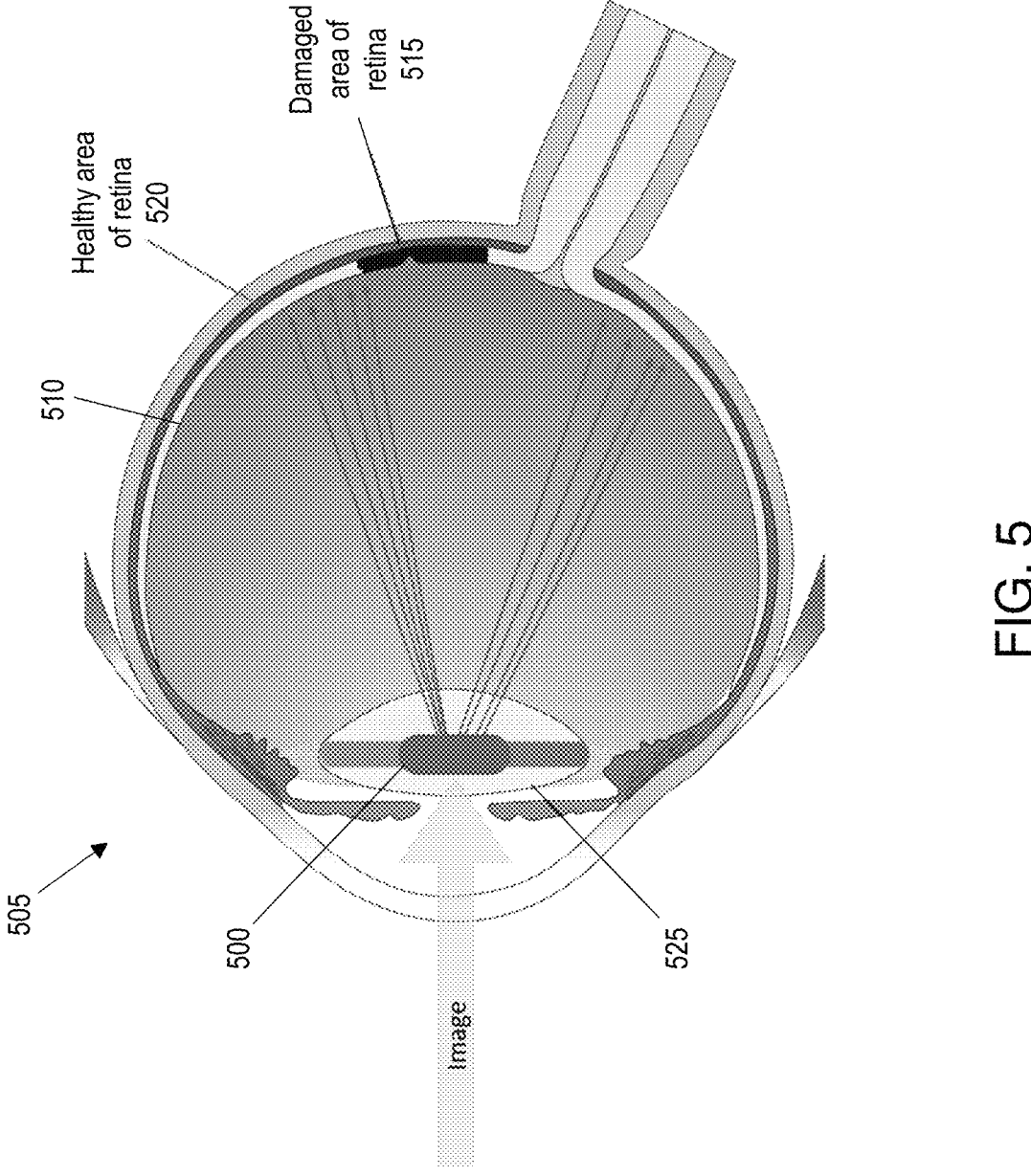
FIG. 5 shows an embodiment of an OPA device implanted in a capsular bag of an eye in accordance with aspects of the invention.
Figure 6:
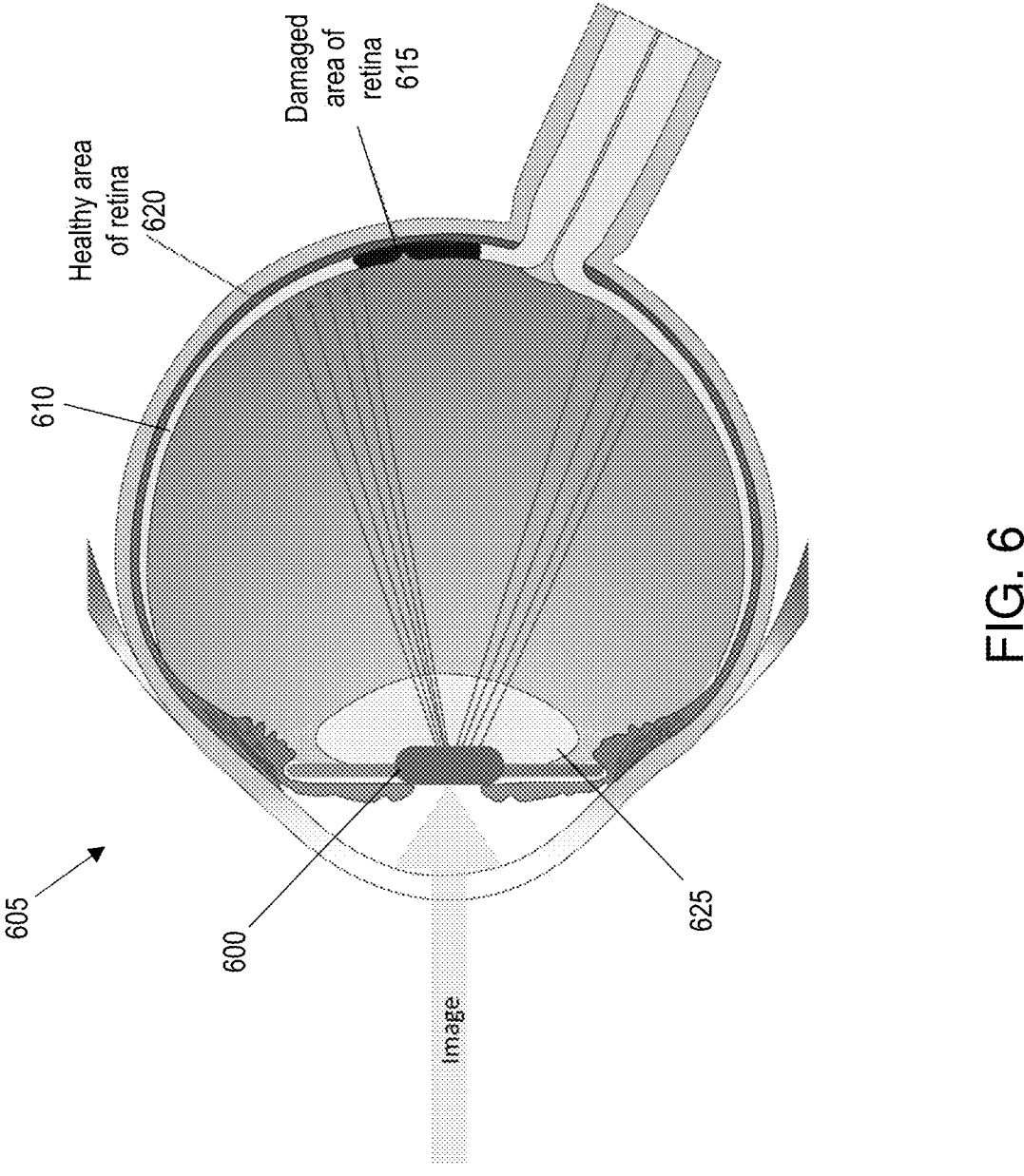
FIG. 6 shows an embodiment of an OPA device implanted in a ciliary sulcus of an eye in accordance with aspects of the invention.
Figure 7:
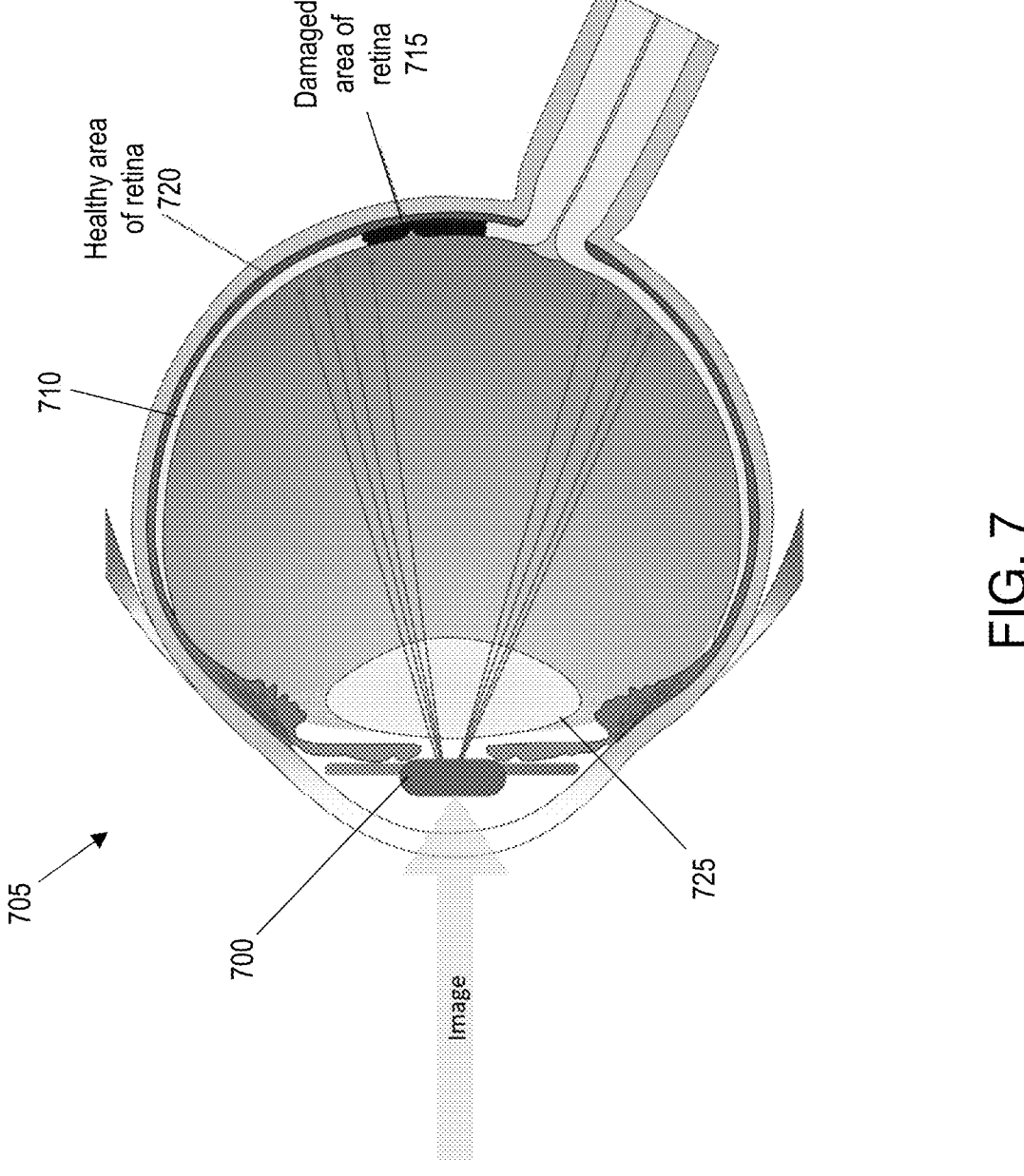
FIG. 7 shows an embodiment of an OPA device implanted in an anterior chamber of an eye in accordance with aspects of the invention.

In an embodiment, the camera, optical signal sources, control electronics, programmable optical array, and power source (e.g., batteries) are all integrated in one device which is surgically implanted in the eye as shown. Exemplary embodiments of implants are shown in FIGS. 5-7.

In embodiments, the surgically implanted chip is wirelessly powered via an inductively coupled primary coil that can be positioned at various locations near the implanted chip, such as for example, on a pair of glasses or on a monocle-style mounting.

Devices according to aspects of the invention allow very detailed (e.g., 1 μm to 50 μm spot size) visible light probing of the retina, including the extreme periphery of functioning retinal tissue. An optical phased array (OPA) implementation of the optical array is well-suited for this application because it has good spot size control and no moving parts.

In embodiments, very detailed (e.g., micron-scaled) maps of functional and non-functional areas of the retina are made by probing/testing precise areas of the retina using an implant in accordance with aspects of the invention.

By being able to probe/test precise areas of the retina, detailed, micron-scaled maps of the functional retina tissue can be created. This mapping provides an advantage over devices that do not utilize mapping, since the mapping permits the inventive devices to precisely target light onto functional areas of the retina. In embodiments, a device is implanted near the front of the eye. This type of surgery is much less invasive and problematic than trying to implant a chip with an array of electrical needle probes or chemical injection ports directly onto the retina surface. Embodiments thus provide a much more practical approach and will allow many more doctors to be able to be trained for the procedure which would be similar to other common surgical eye procedures/implants.

In one embodiment, a wirelessly powered and programmable device including an integrated CCD, control electronics, and OPA is surgically implanted in the eyeball as shown, for example, in FIG. 7. In one example, the device is hermetically sealed and completely self-contained.

Devices according to aspects of the invention may be used diagnostically, e.g., for creating detailed functional retinal tissue maps. Devices according to aspects of the invention may be used therapeutically, e.g., for image construction and projection onto functional retinal tissue in real time.

In embodiments, there is a surgically implanted integrated device that includes a camera, control electronics, programmable circuitry, and an optical phased array device for retinal image generation. In embodiments, the device is used for mapping healthy (also called functional) retina tissue and unhealthy (also called damaged or non-functional) retina tissue. In embodiments, the device is used for image projection onto healthy retina tissue. In embodiments, the device is used to project eyeball-motion directed images selectively onto the healthy portions of retina tissue according to a map. The device may have wirelessly powered variants. The device may be used to perform a method of mapping healthy and unhealthy areas of the retina.

Figure 1:
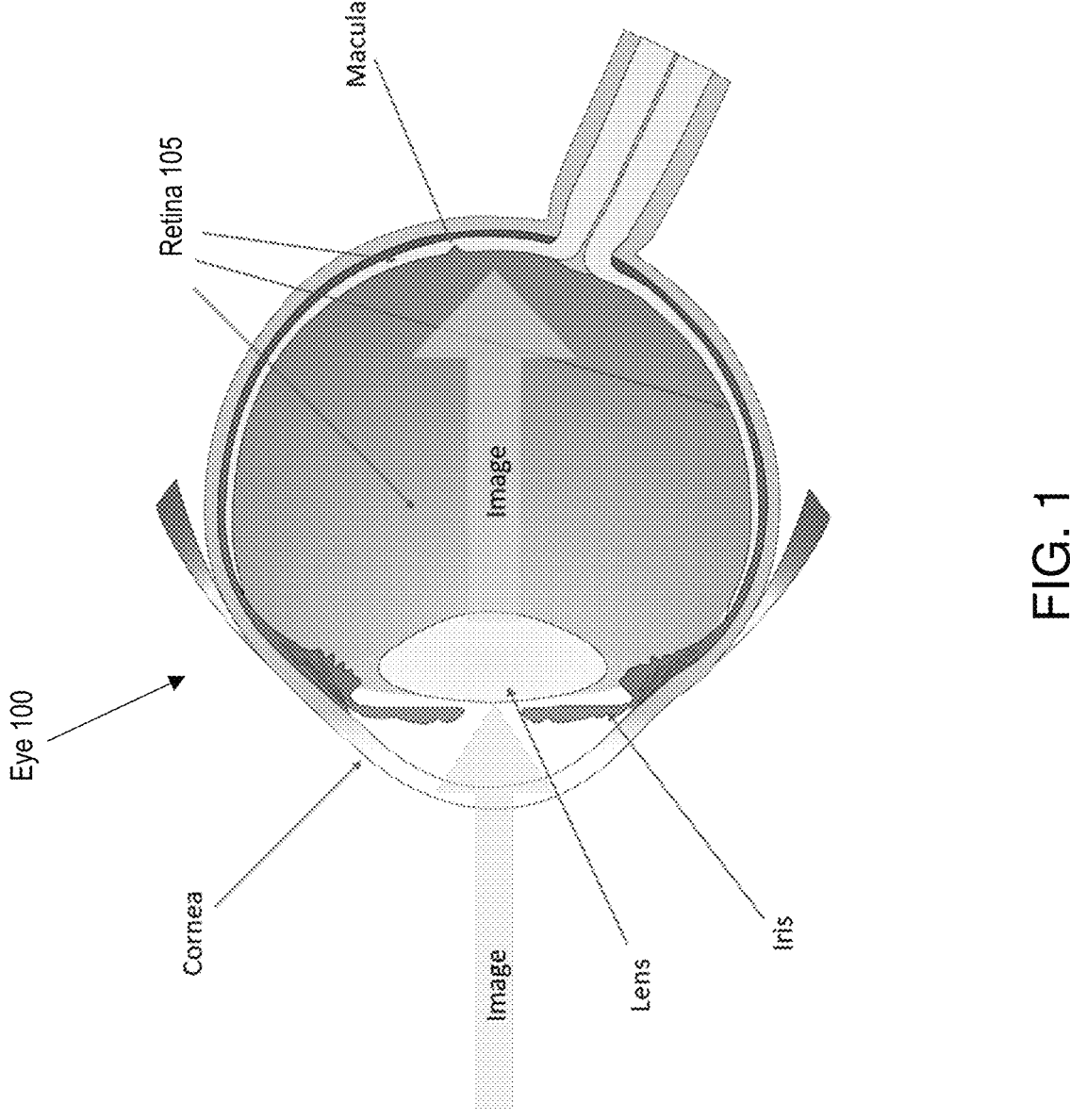
FIG. 1 shows a diagram of a healthy eye.

FIG. 1 shows a diagram of a healthy eye 100. As shown in FIG. 1, an image in the form of visible light enters the cornea and is focused onto the lens and then finally onto the macula e.g., (central portion of the retina 105) which allows for clear vision.

Figure 2:
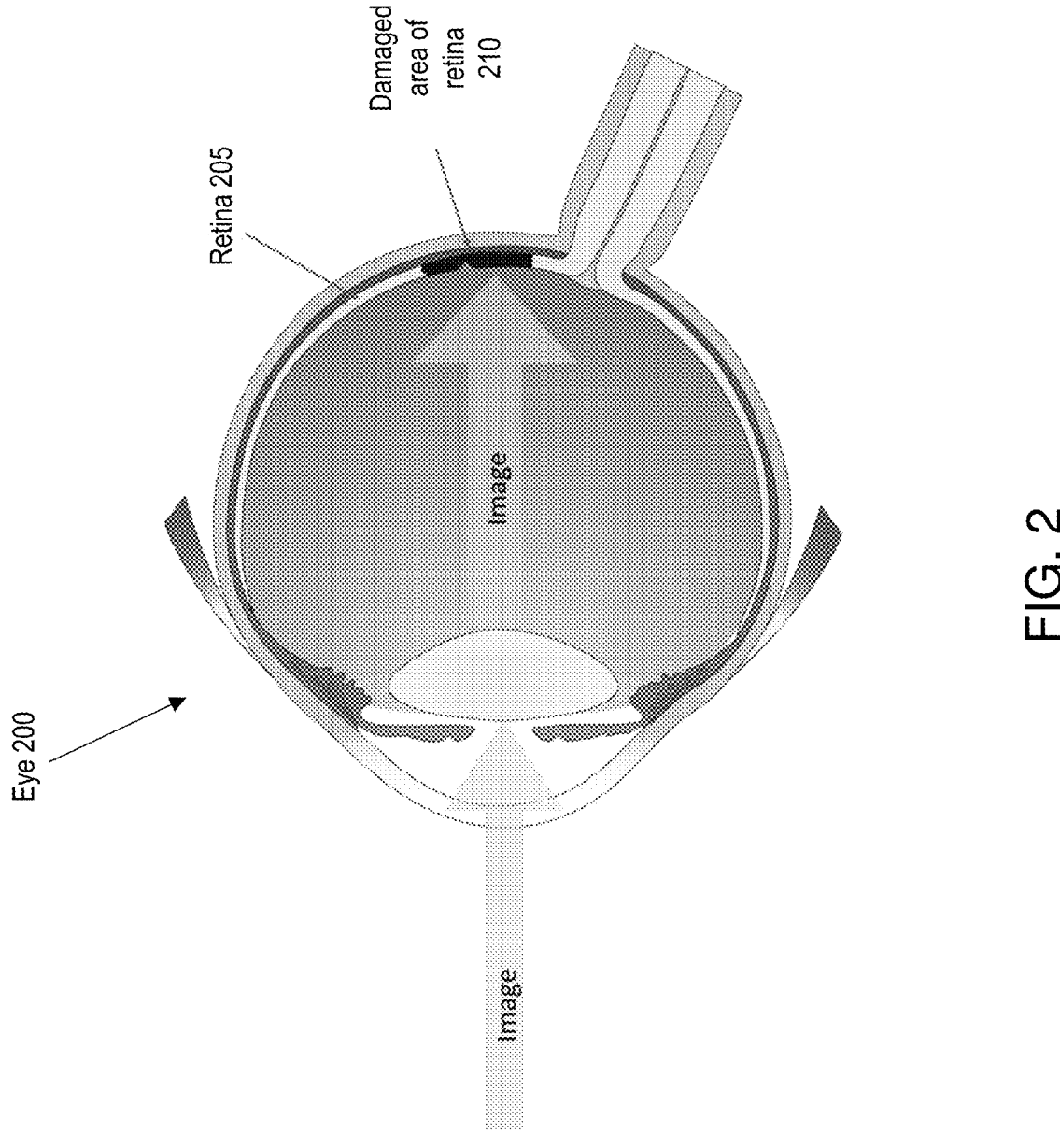
FIG. 2 shows a diagram of a damaged eye.

FIG. 2 shows a diagram of a damaged eye 200. As shown in FIG. 2, retinal scarring in the macula (e.g., macular degeneration) results in a damaged area 210 of the retina 205 that causes loss of central vision (e.g., scotoma). Implementations of the invention seek to take advantage of the still healthy areas of the retina, e.g., not including the damaged area, to help patients regain significant visual function.

Figures 3A, 3B:
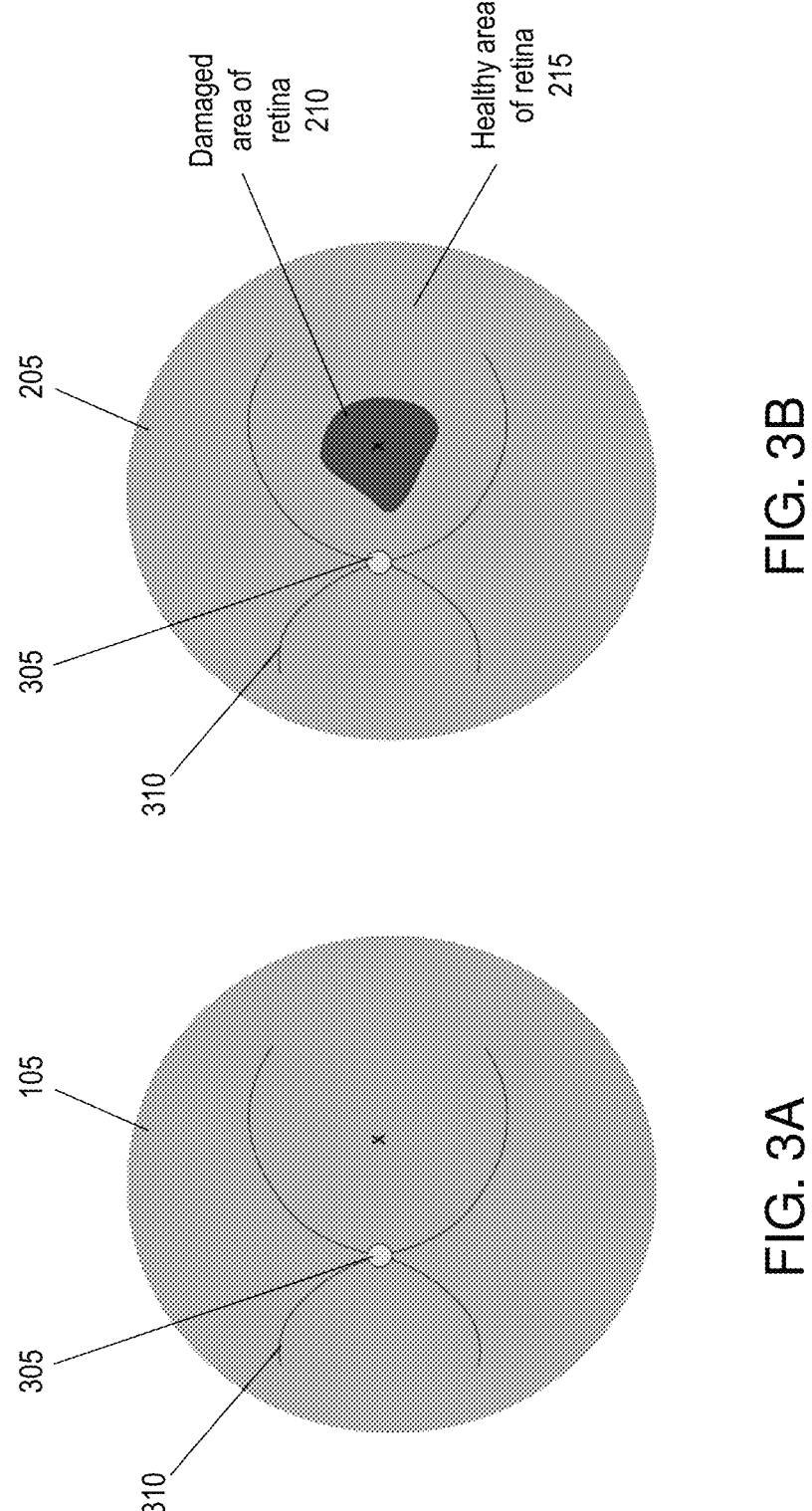
FIG. 3A shows a diagram of a healthy retina corresponding to the eye of FIG. 1.
FIG. 3B shows a diagram of a damaged retina corresponding to the eye of FIG. 2.

FIG. 3A shows a diagram of a healthy retina 105 corresponding to the eye 100 of FIG. 1. Also shown are the optic nerve/disc 305 and retinal veins/arteries 310. As shown in FIG. 3A, the retina 105 does not have a damaged portion and, thus, provides normal central vision for the person.

FIG. 3B shows a diagram of a damaged retina 205 corresponding to the eye 200 of FIG. 2. Also shown are the optic nerve/disc 305 and retinal veins/arteries 310. As shown in FIG. 3B, the retina 205 includes a damaged area 210 that produces a large central scotoma in the person's vision. As shown in FIG. 3B, the retina 205 includes undamaged area 215 around the damaged area 205.

Figures 4A, 4B:
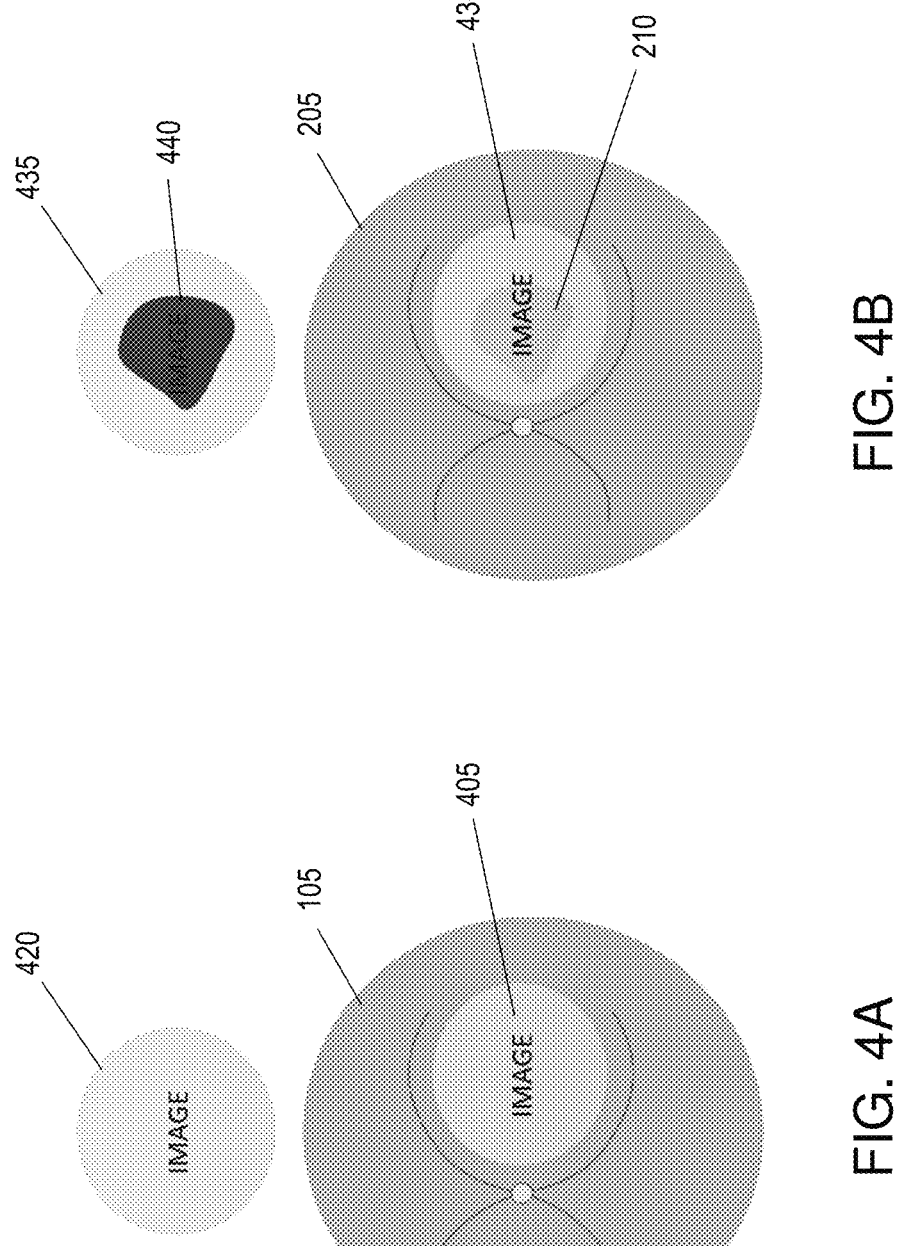
FIG. 4A shows a diagram of an image that is incident on the healthy retina of FIG. 3A and the resulting view to the person.
FIG. 4B shows a diagram of an image that is incident on the damaged retina of FIG. 3B and the resulting view to the person.

FIG. 4A shows a diagram of an image 405 (e.g., visible light) that is incident on the healthy retina 105 of FIG. 3A. FIG. 4A illustrates a view 420 of what this person sees based on the image 405 being incident on the retina 105. As shown in FIG. 4A, the view 420 of what this person sees is a normal view without any scotoma.

FIG. 4B shows a diagram of an image 430 (e.g., visible light) that is incident on the damaged retina 205 of FIG. 3B. FIG. 4B illustrates a view 435 of what this person sees based on the image 430 being incident on the retina 205 having the damaged area 210. As shown in FIG. 4B, the view 435 of what this person sees has a large central scotoma 440, represented in this case by a dark or fuzzy spot in an otherwise normal view.

FIG. 5 shows an embodiment of an OPA device 500 implanted in a capsular bag of an eye in accordance with aspects of the invention. As shown in FIG. 5, the eye 505 includes a retina 510 that has a damaged area 515 and a healthy area 520, e.g., similar to the retina 205 shown in FIGS. 3B and 4B. The eye 505 also includes a capsular bag 525 which normally contains the lens, e.g., the human crystalline lens. In accordance with aspects of the invention, the human lens is removed and replaced with the OPA device 500 that is configured to receive an image (e.g., visible light) from outside the eye and project the image onto the healthy area 520 of the retina 510 using beam steering provided by an OPA in the OPA device 500. By projecting the image onto the healthy area 520 of the retina 510 and avoiding projecting the image onto the damaged area 515, the implanted OPA device 500 provides this person with a view that eliminates or greatly reduces the scotoma that this person would otherwise have if the OPA device 500 were not present.

The OPA device 500 may be implanted in the capsular bag 525 after primary cataract surgery or as an intraocular lens exchange with intact posterior capsule. An exemplary method for implanting the OPA device 500 in the capsular bag 525 includes: making a 6-8 mm incision at the limbus or slightly posterior (1-2 mm) posterior to the limbus; through a pharmacologically dilated pupil, making a 6-8 mm diameter opening in the anterior capsular bag; and removing the human crystalline lens entirely in an extra capsular fashion such as phacoemulsification. If the eye is pseudophakic with an intact posterior capsule, then intraocular lens is dissected free of its capsular attachment and removed from the eye. The capsular opening is then widened if necessary. The OPA device 500 is then placed through the primary incision and into the capsular bag. The haptics of the OPA device 500 keep the implant centered in the capsular bag as it heals and creates a fibrotic membrane to stabilize the implant, and place the OPA device 500 directly in the visual axis for the purpose of projecting the central image onto the healthiest part of the retina as close to the damaged area 515 as possible. In embodiments where the OPA device 500 has external wiring, the wires coming from the OPA device 500 may be placed anterior to the anterior capsule and posterior to the iris and routed to the limbus, for example, through a 30 or 27 gauge temporal sclerotomy 2-3 mm posterior to the limbus. The wires may be left subconjunctival to prevent foreign body sensation. All support material may be removed, and the primary wound may be closed with sutures if needed. The OPA device 500 is thus held inside the capsular bag 525. Over time, the bag fibrosis around the haptics of the implant is stable in place.

FIG. 6 shows an embodiment of an OPA device 600 implanted in a ciliary sulcus of an eye in accordance with aspects of the invention. The ciliary sulcus is a small space between the posterior surface of the iris base and the anterior surface of the ciliary body. As shown in FIG. 6, the eye 605 includes a retina 610 that has a damaged area 615 and a healthy area 620, e.g., similar to the retina 205 shown in FIGS. 3B and 4B. The eye 605 also includes a capsular bag 625 which normally contains the lens, e.g., the human crystalline lens. In accordance with aspects of the invention, the human lens is removed and the OPA device 600 is inserted into the ciliary sulcus. The OPA device 600 is configured to receive an image (e.g., visible light) from outside the eye and project the image onto the healthy area 620 of the retina 610 using beam steering provided by an OPA in the OPA device 600. By projecting the image onto the healthy area 620 of the retina 610 and avoiding projecting the image onto the damaged area 615, the implanted OPA device 600 provides this person with a view that eliminates or greatly reduces the scotoma that this person would otherwise have if the OPA device 600 were not present.

The OPA device 600 may be implanted in the ciliary sulcus after primary cataract surgery with compromised posterior capsule or as an intraocular lens exchange with open posterior capsule. An exemplary method for implanting the OPA device 600 in the ciliary sulcus includes: making a 6-8 mm incision at the limbus or slightly posterior (1-2 mm) posterior to the limbus; through a pharmacologically dilated pupil, making a 6-8 mm diameter opening in the anterior capsular bag; and removing the human crystalline lens entirely in an extra capsular fashion such as phacoemulsification. A thorough anterior vitrectomy is performed in the presence of a posterior capsule defect. If the eye is pseudophakic with an open posterior capsule, the intraocular lens is dissected free of its capsular attachment and removed from the eye. The capsular opening is then widened if necessary and a thorough anterior vitrectomy is performed. The OPA device 600 is placed through the primary incision and into the ciliary sulcus on the anterior aspect of the capsular bag, directly posterior to the iris. The haptics of the OPA device 600 will keep the implant centered in the ciliary sulcus to stabilize the implant and place the OPA device 600 directly in the visual axis for the purpose of projecting the central image onto the healthiest part of the retina as close to the damaged area 615 as possible. In embodiments where the OPA device 600 has external wiring, the wires coming from the OPA device 600 may be placed anterior to the anterior capsule and posterior to the iris and routed to the limbus, for example, through a 30 or 27 gauge temporal sclerotomy 2-3 mm posterior to the limbus. The wires may be left subconjunctival to prevent foreign body sensation. All support material may be removed, and the primary wound may be closed with sutures if needed. The OPA device 600 haptics rest in the ciliary sulcus posterior to the iris and directly anterior to the capsular bag, which stabilizes the lens.

FIG. 7 shows an embodiment of an OPA device 700 implanted in an anterior chamber of an eye in accordance with aspects of the invention. As shown in FIG. 7, the eye 705 includes a retina 710 that has a damaged area 715 and a healthy area 720, e.g., similar to the retina 205 shown in FIGS. 3B and 4B. The eye 705 also includes a capsular bag 725 which normally contains the lens, e.g., the human crystalline lens. In accordance with aspects of the invention, the human lens is removed and the OPA device 700 is inserted into the anterior chamber of an eye, e.g., anterior to the iris. The OPA device 700 is configured to receive an image (e.g., visible light) from outside the eye and project the image onto the healthy area 720 of the retina 710 using beam steering provided by an OPA in the OPA device 700. By projecting the image onto the healthy area 720 of the retina 710 and avoiding projecting the image onto the damaged area 715, the implanted OPA device 700 provides this person with a view that eliminates or greatly reduces the scotoma that this person would otherwise have if the OPA device 700 were not present.

The OPA device 700 may be implanted in the anterior chamber after primary cataract surgery with no capsular support or as an intraocular lens exchange with no capsular support. An exemplary method for implanting the OPA device 700 in the anterior chamber includes: making a 6-8 mm incision at the limbus or slightly posterior (1-2 mm) posterior to the limbus; through a pharmacologically dilated pupil, making a 6-8 mm diameter opening in the anterior capsular bag; and removing the human crystalline lens entirely in an extra capsular fashion such as phacoemulsification. A thorough anterior vitrectomy is performed in the absence of sufficient capsular support. If the eye is pseudophakic with an open posterior capsule, the intraocular lens is dissected free of its capsular attachment and removed from the eye, and a thorough anterior vitrectomy is performed in the absence of sufficient capsular support. Miosis of the pupil may be performed to provide support for the OPA device 700. The OPA device 700 is then placed through the primary incision and into the anterior chamber directly anterior to the iris. The haptics of the OPA device 700 are seated into the anterior chamber angle to stabilize the implant and place the OPA device 700 directly in the visual axis for the purpose of projecting the central image onto the healthiest part of the retina as close to the damaged area 715 as possible. A small peripheral iridotomy may be performed to prevent pupillary block. In embodiments where the OPA device 700 has external wiring, the wires coming from the OPA device 700 may be placed anterior to the anterior capsule and posterior to the iris and routed to the limbus, for example, through a 30 or 27 gauge temporal sclerotomy 2-3 mm posterior to the limbus. The wires may be left subconjunctival to prevent foreign body sensation. All support material may be removed, and the primary wound may be closed with sutures if needed.

Figure 8:
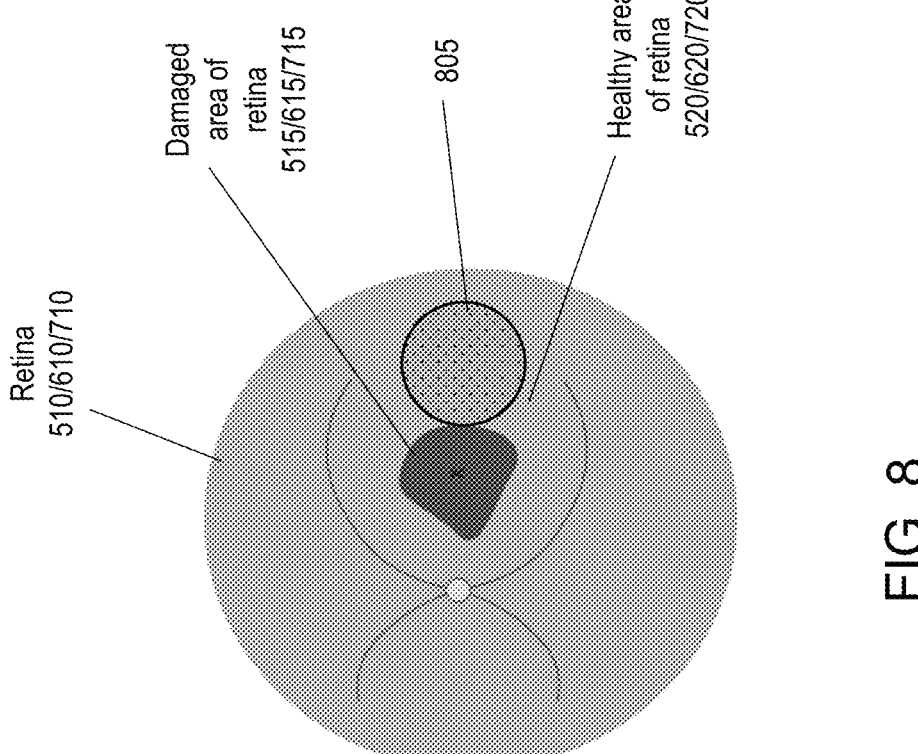
FIG. 8 shows a diagram of an exemplary projection of an image on a retina by an OPA device in accordance with aspects of the invention.

FIG. 8 shows a diagram of an exemplary projection of an image on a retina 510/610/710 by an OPA device 500/600/700 in accordance with aspects of the invention. As described with respect to FIGS. 5-7, the OPA device 500/600/700 receives an incoming image, in the form of visible light from outside the eye, and projects the image onto a healthy area 520/620/720 of the retina while avoiding projecting the image onto the damaged area 515/615/715. FIG. 8 shows the projection area 805 relative to the damaged area 515/615/715. The shape of the projection area 805 in FIG. 8 is illustrative, and the projection area 805 may have other shapes different than what is shown in FIG. 8.

Figure 9:
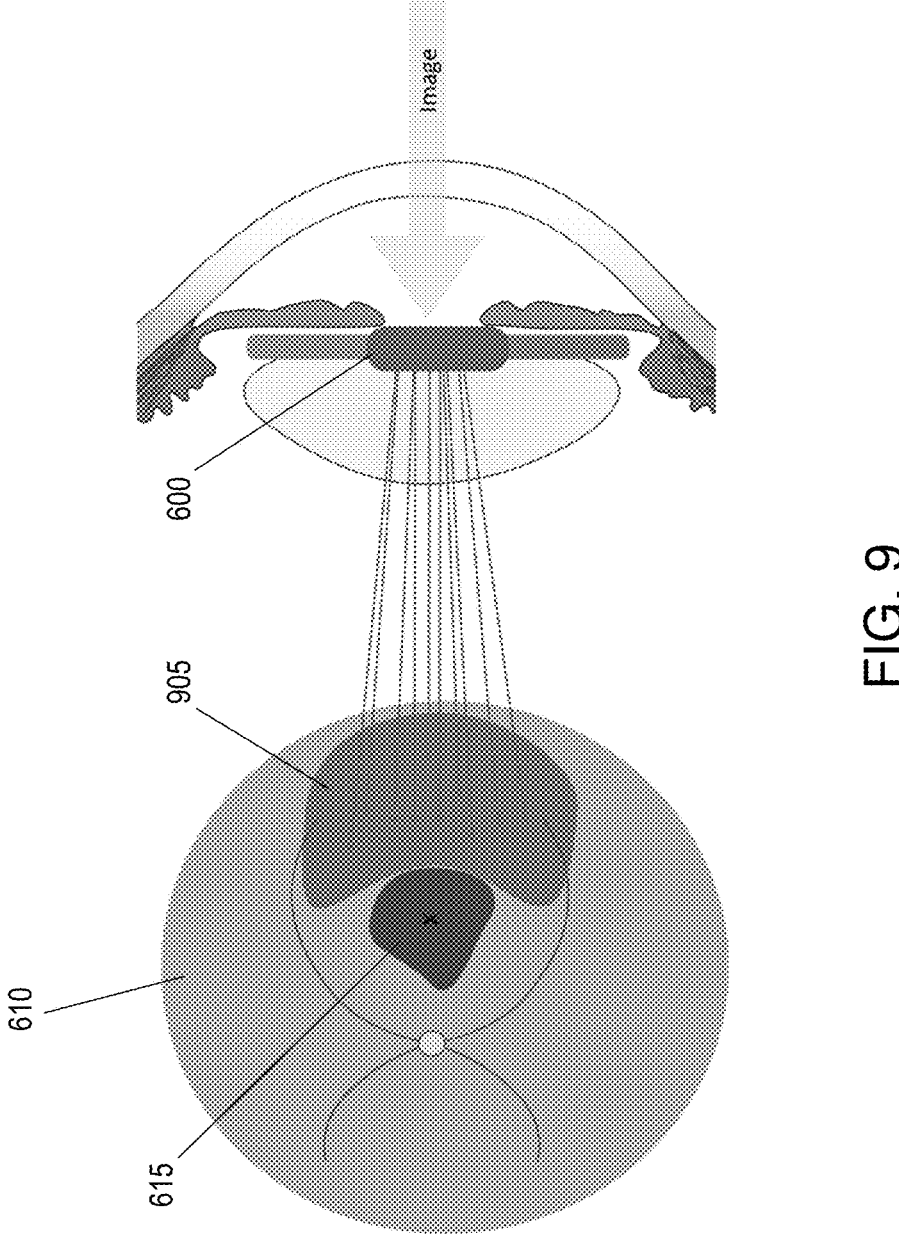
FIG. 9 shows a diagram of an exemplary projection of an image on a retina by an OPA device in accordance with aspects of the invention.

FIG. 9 shows a diagram of an exemplary projection of an image on a retina by an OPA device 600 in accordance with aspects of the invention. As described with respect to FIG. 6, the OPA device 600 receives an incoming image, in the form of visible light from outside the eye, and projects the image onto a healthy area of the retina while avoiding projecting the image onto the damaged area 615. FIG. 9 shows the projection area 905 relative to the damaged area 615. Specifically, the OPA device 600 takes the central image and shifts the projection onto the adjacent healthy area of the retina. In this manner, the healthy area of the retina adjacent to the damaged area of the retina can be used for central vision. The shape of the projection area 905 in FIG. 9 is illustrative, and the projection area 905 may have other shapes different than what is shown in FIG. 9. Although FIG. 9 only shows the OPA device 600, it should be understood that the OPA device 500 and the OPA device 700 may function in a similar manner, with a difference being where the different devices 500, 600,700 are implanted in the eye.

Figure 10:
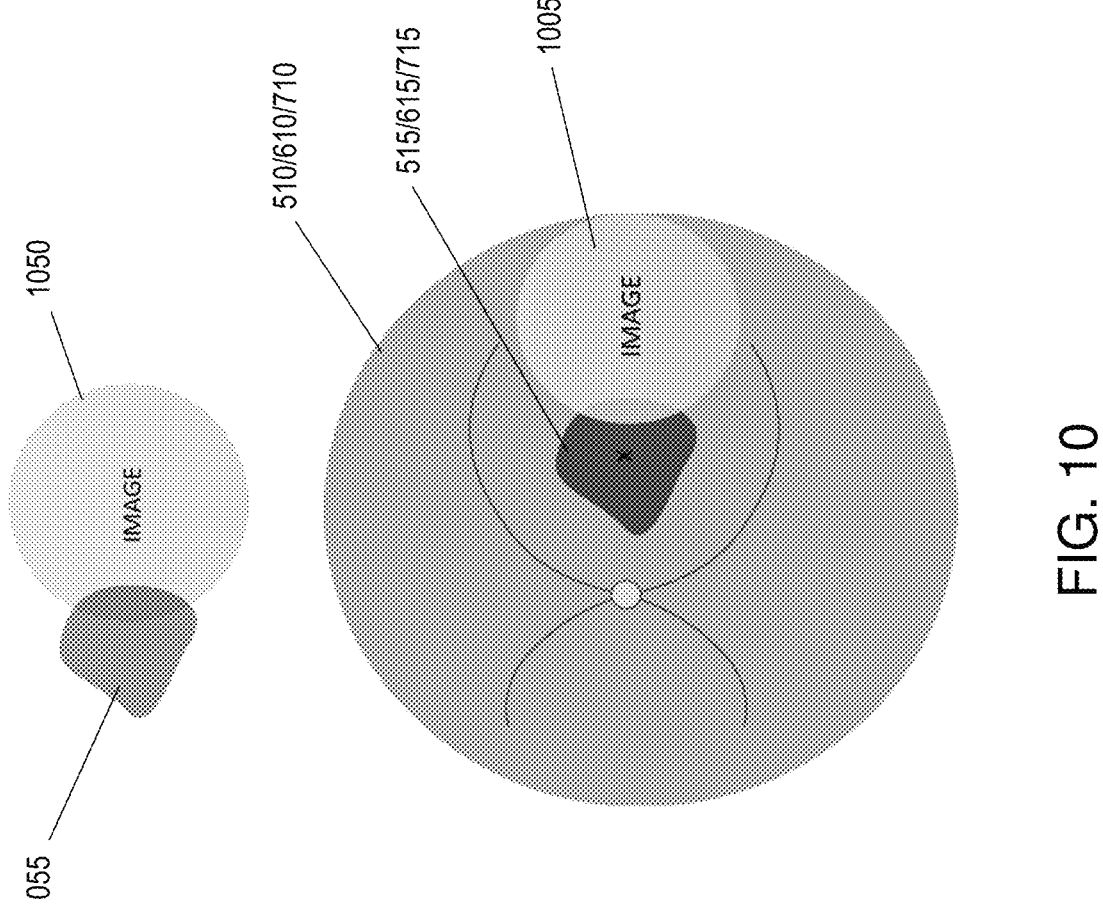
FIG. 10 shows a diagram of an image projected on the healthy area of the retina by an OPA device in accordance with aspects of the invention, and a view of what the person sees based on the image being projected in the manner shown.

FIG. 10 shows a diagram of an image 1005 projected on the healthy area of the retina 510/610/710 by an OPA device 500/600/700 in accordance with aspects of the invention, and a view 1050 of what the person sees based on the image being projected in the manner shown. As described herein, the OPA device 500/600/700 projects the image onto the healthy area of the retina adjacent to the damaged area 515/615/715 of the retina. In this manner, the view 1050 of what the person sees has the scotoma 1055 shifted away from the center, such that the person can now see central visual details unimpeded by the scotoma. Comparing the view 1050 of FIG. 10 to the view 435 of FIG. 4B, it is evident that the OPA device 500/600/700 provides a vast improvement in central vision for the person.

FIG. 11 shows an exemplary point-to-point pixelated mapping from a 2D directionally programmable optical array 1101 to a retina 1102 optical nerve surface in accordance with aspects of the invention. In embodiments, individual elements of the array 1101 are mapped to locations on the retina 1102. The OAP device 500/600/700 may use the mapping defined in the array to control the beam steering to project the image onto healthy areas of the retina and avoid projecting onto the damaged areas of the retina.

FIG. 12 shows an exemplary point-to-point pixelated mapping from a 2D directionally programmable optical array 1201 to a retina 1202 optical nerve surface in accordance with aspects of the invention. In embodiments, the OPA device 500/600/700 produces a moving spot that is dynamically swept across retina. Optical phased arrays operating in quasi near field regime (e.g., within a few wavelengths of the array surface) with spot sizes on the order of 10 μm are achievable. This spot size can be used to create high-definition quality pixel sizes on the retina. The visible wavelength is between about 380 nm and 750 nm and the eyeball is about 1 to 2 inches long, which is about 25 mm to 50 mm, which is about 30 to 130 wavelengths long, which means that the image projected by the OPA device 500/600/700 can be close to the near field.

Figure 13:
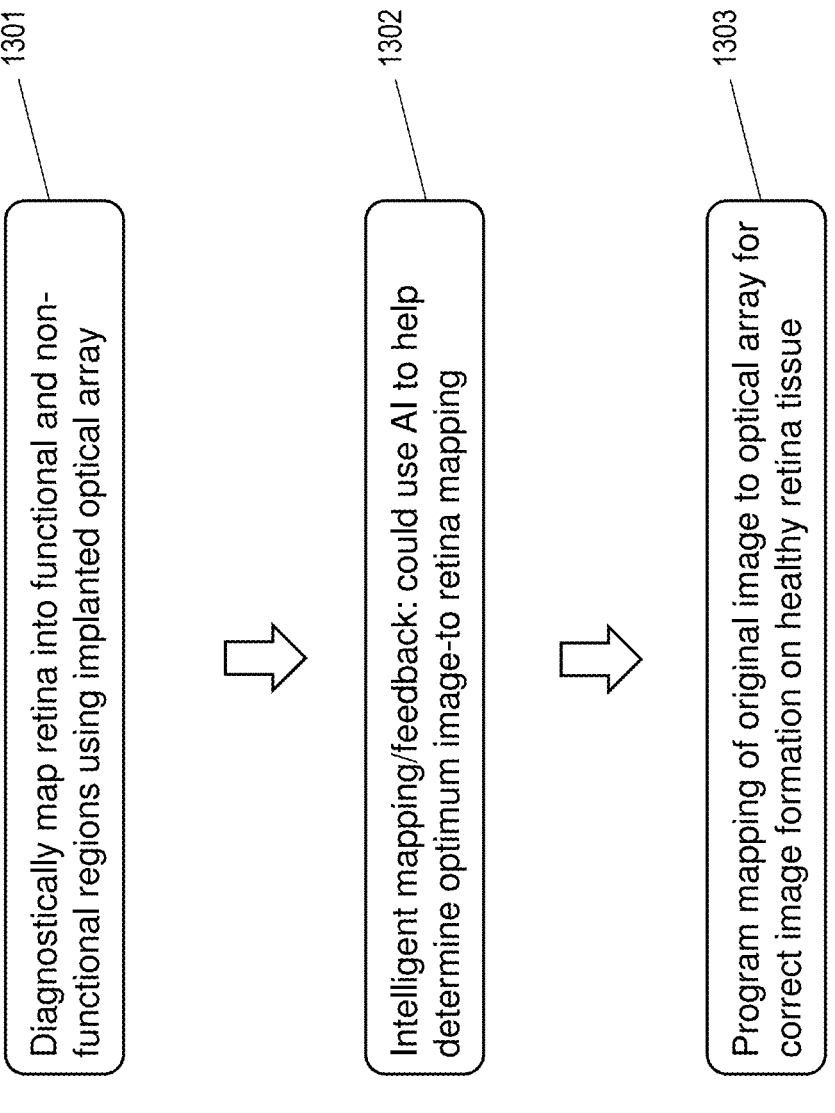
FIG. 13 shows a flowchart of an exemplary method in accordance with aspects of the invention.

FIG. 13 shows a flowchart of an exemplary method in accordance with aspects of the invention. At step 1301, the implanted OPA device 500/600/700 is used to diagnostically map a retina (of the eye in which the device is implanted) into functional and non-functional regions, e.g., healthy areas and damaged areas. This may include projecting an image onto a mapped location on the retina and receiving feedback from the person as to whether they can or cannot see the image clearly. This is repeated for all locations on the 2D array that are mapped to locations on the retina. In this manner, the implanted OPA device 500/600/700 can be used to map the areas of the retina.

Step 1302 comprises using artificial intelligence to optimize the mapping that was determined at step 1301. The shape of the damaged areas and healthy areas of each person's retina will be unique and irregular. In embodiments, an optimum mapping of a regular 2D grid array of input pixels to the irregular healthy regions is determined using artificial intelligence. For example, an artificial neural network may be used to optimize a map of the regular input pixel grid to the irregular healthy retinal tissue, while minimizing the radius from the center of the retina, and while also seeking to maximize the symmetry of the pixel projection around the center. These sorts of constrained mapping tasks are well suited for AI in general and artificial neural networks specifically. The mapping here may take into account complex procedures using artificial neural networks that not only map to healthy retina tissue, but also take into account brain plasticity for image reconstruction.

Step 1303 involves program mapping of an original image to the optical array for correct image formation on the healthy area of the retina. In embodiments, the array that defines the mapping is stored in a programmable circuit of the OPA device 500/600/700. In embodiments, when in use, the OPA device 500/600/700 uses the mapping defined in the array to control the phase shifting of the OPA elements to cause beam steering that projects the image onto the healthy areas of the retina as defined in the mapping.

Figure 14B:
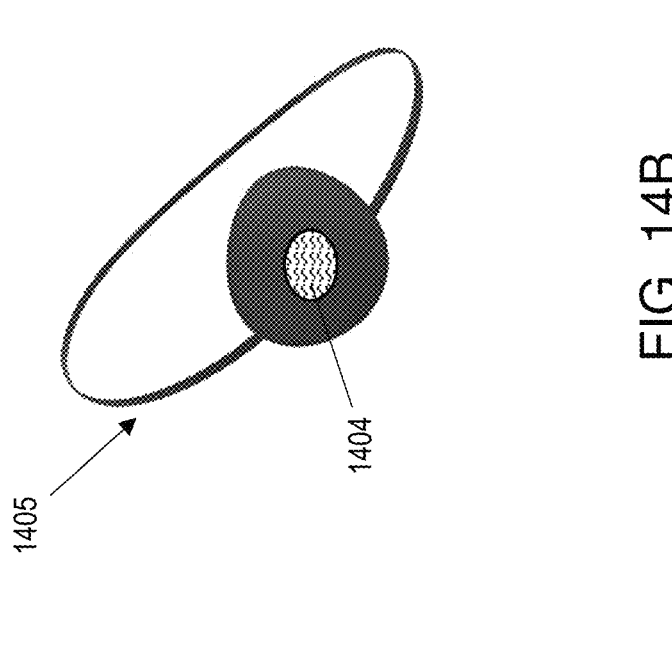
FIG. 14B shows an exemplary location on an eyepatch for coils that may be used to wirelessly charge the OPA device in accordance with aspects of the invention.
Figure 14A:
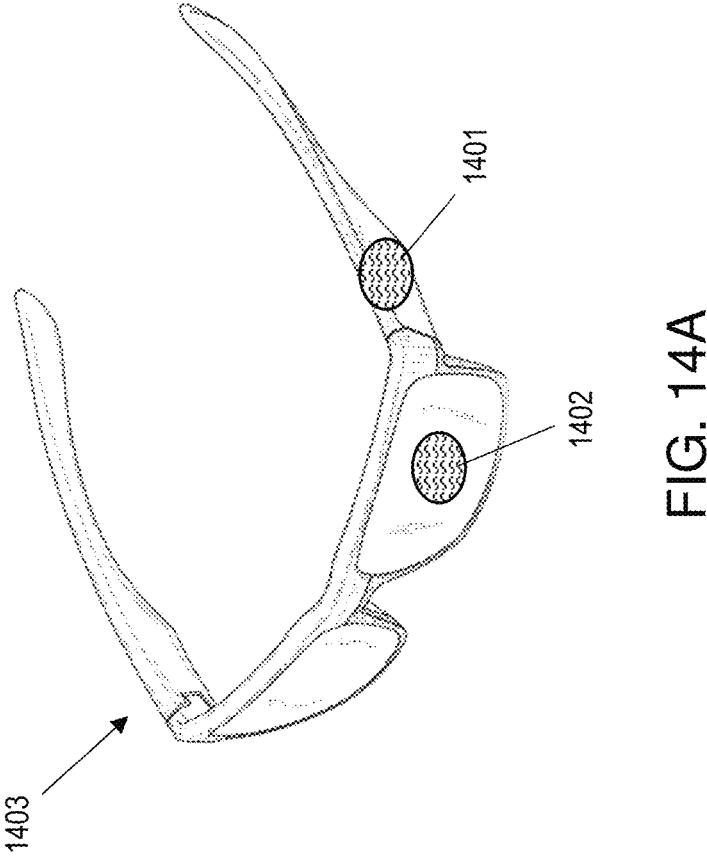
FIG. 14A shows exemplary locations on eyeglasses for coils that may be used to wirelessly charge the OPA device in accordance with aspects of the invention.

FIG. 14A shows exemplary locations 1401, 1402 on eyeglasses 1403 for coils that may be used to wirelessly charge the OPA device 500/600/700 that is implanted in a person's eye. FIG. 14B shows an example of a location 1404 on an eyepatch 1405 for coils that may be used to wirelessly charge the OPA device 500/600/700 that is implanted in a person's eye. The external charging system is not limited to eyeglasses or an eye patch, and can be on other devices, such as a contact lens. The external charging system itself can be rechargeable. For example, a contact lens may comprise a battery that is wirelessly rechargeable, e.g., from a docking station, and that same contact lens can include control circuitry and charging coils that utilize power from the battery in the contact lens to inductively charge the OPA device 500/600/700 when the contact lens is within range of the OPA device.

Figure 15:
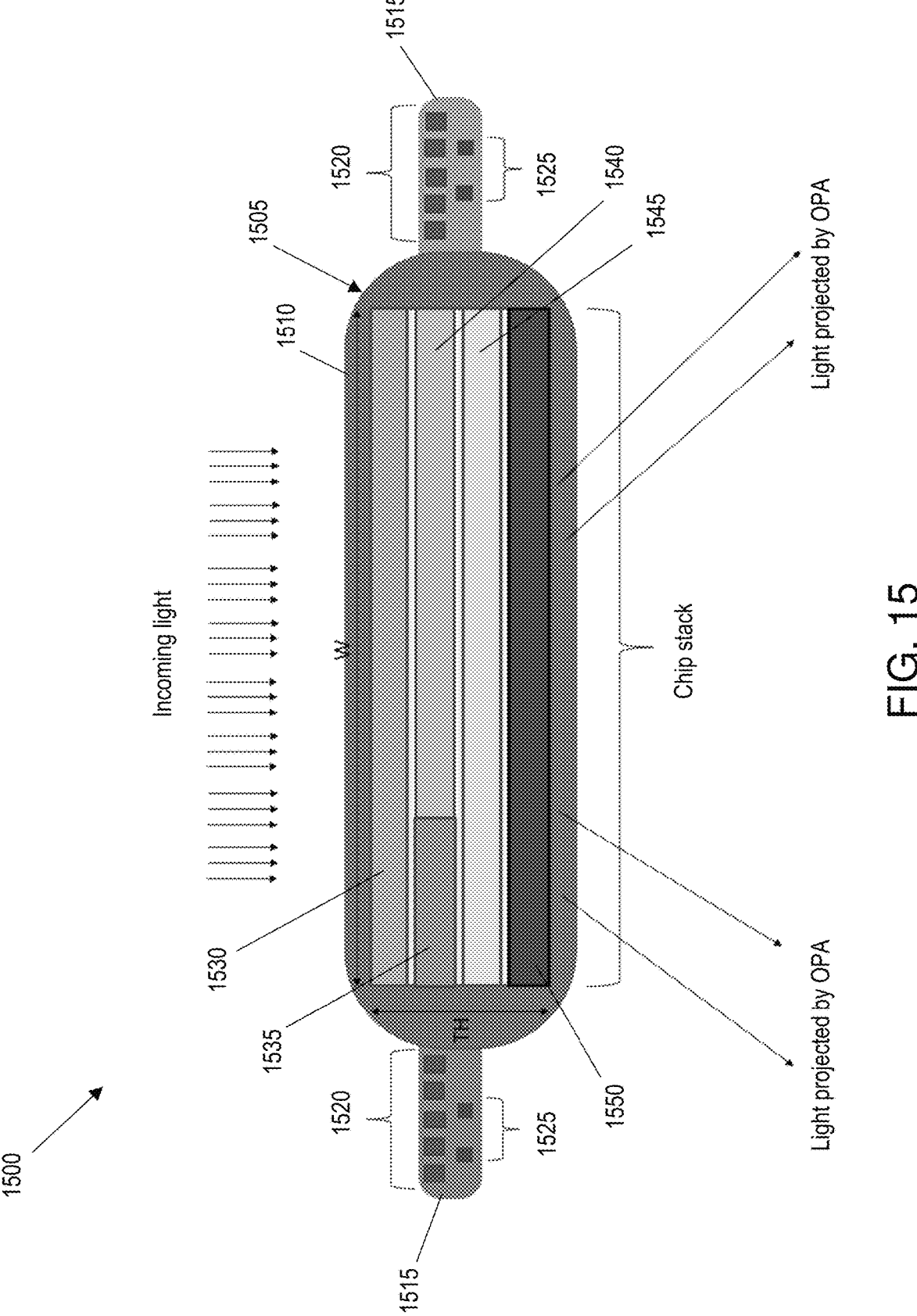
FIG. 15 shows an embodiment of an OPA device in accordance with aspects of the invention.

FIG. 15 shows an embodiment of an OPA device 1500 in accordance with aspects of the invention. The OPA device 1500 may be used as the OPA devices 500/600/700 described herein. In embodiments, the OPA device 1500 includes a body 1505 that has a central portion 1510 and haptics 1515. The body 1505 may be made in the form of a single piece lens composed of materials such as acrylic and/or silicon lens material. In embodiments, the body 1505 comprises two haptics 1515 in the form of wings or tabs that each extend outward from the central portion 1510.

In embodiments, the OPA device 1500 comprises inductive coupling coils 1520, a wireless communication antenna 1525, an imaging system 1530, a power source 1535, control circuitry 1540, optical source generation circuitry 1545, and an optical phased array (OPA) 1550. In embodiments, the inductive coupling coils 1520 and wireless communication antenna 1525 are embedded in one or both haptics 1515, and the remaining elements 1530, 1535, 1540, 1545, 1550 are integrated in chip stack contained in the body 1505. As shown in FIG. 15, the imaging system 1530 is at a first side of the chip stack such that it can receive incoming light from outside the eye, and the OPA 1550 is at a second side of the chip stack opposite the first side of the chip stack such that the OPA 1550 can project an image onto the retina inside the eye in which the OPA 1500 device is implanted. In embodiments, the imaging system 1530 receives incoming light from outside the eye and provides input to the control circuitry 1540 based on the received light, and the control circuitry 1540 provides electronic control signals to the optical source generation circuitry 1545 and the OPA 1550 based on the input received from the imaging system 1530. In this manner, the OPA 1550 is controlled to reproduce an image received by the imaging system 1530 via projection onto the mapped areas of the retina.

Figure 16:
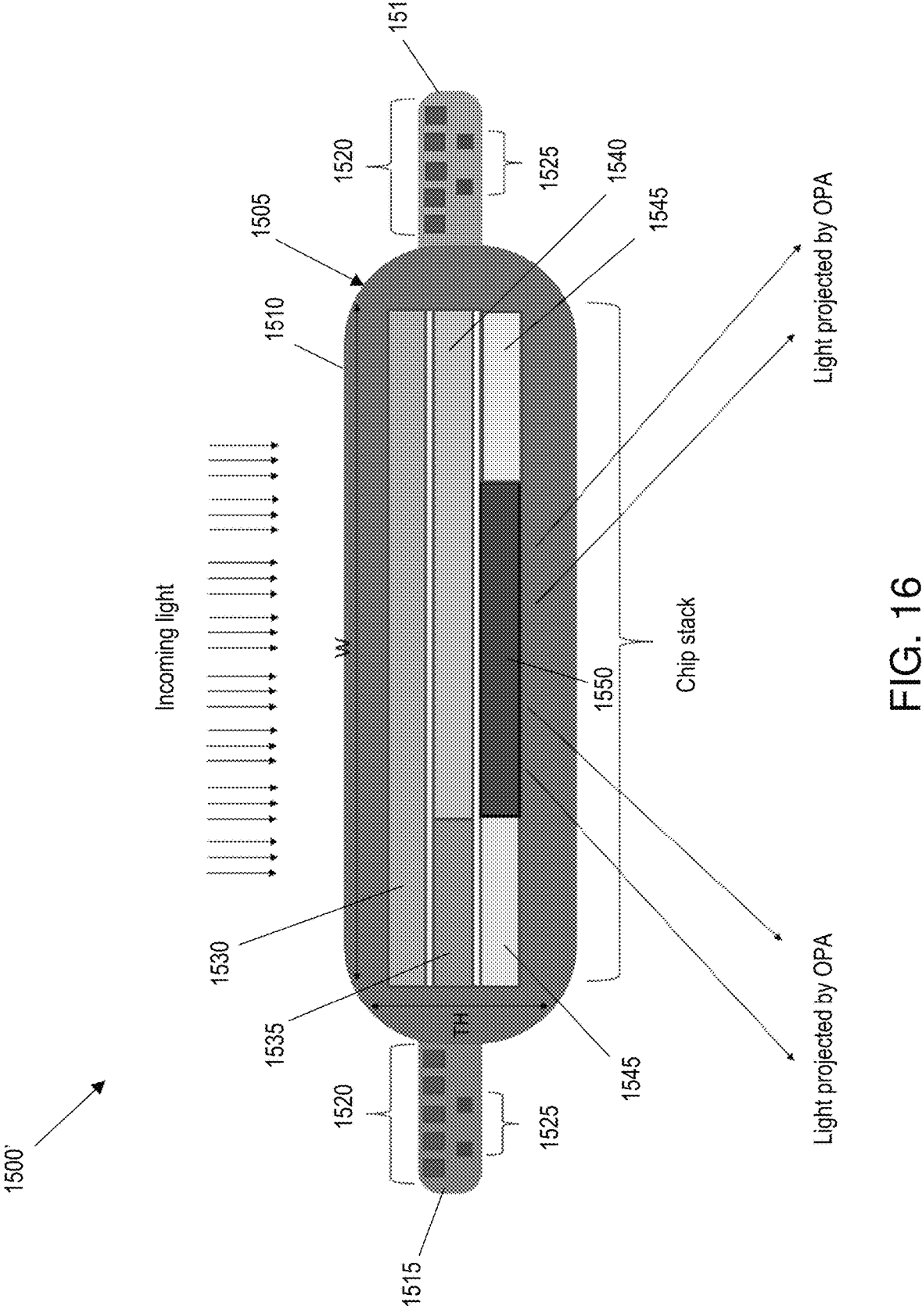
FIG. 16 shows an embodiment of an OPA device in accordance with aspects of the invention.

FIG. 15 shows an embodiment of the OPA device 1500 in which the imaging system 1530, power source 1535, control circuitry 1540, optical source generation circuitry 1545, and OPA 1550 are arranged in four layers of a chip stack. FIG. 16 shows an embodiment of the OPA device 1500' in which the imaging system 1530, power source 1535, control circuitry 1540, optical source generation circuitry 1545, and OPA 1550 are arranged in three layers of a chip stack. Other arrangements of these elements in a chip or chip stack may be used so long as the imaging system 1530 is positioned to receive incoming light and the OPA 1550 is positioned to project an image onto the retina inside the eye in which the OPA device is implanted.

The following description of the OPA device applies to both the OPA device 1500 of FIG. 15 and the OPA device 1500' of FIG. 16 unless indicated otherwise. The imaging system 1530 may comprise a CCD/imaging chip. The power source 1535 may comprise a battery that is rechargeable either via wired connection or wirelessly. The control circuitry 1540 may comprise a CMOS/analog/OPA control/wireless chip that is configured to control operation of the OPA device. The optical source generation circuitry 1545 may comprise an optical source/generation chip. The OPA 1550 may comprise components of an on-chip optical phase array including but not limited to: splitters, waveguides, phase shifters, amplifiers, and emitting elements.

The OPA device 1500/1500' may be composed of sub-circuits which may be on disparate chip materials and made with disparate technologies, such as Si, InP, GaAs, Liquid Crystal, etc. This integrated system can be stacked in as shown in FIGS. 15 and 16, with the connections between circuit elements being formed using BGA/C4/micro-BGA, through substrate (or silicon) vias (TSVs), and micro-TSVs. Physical connections between layers can be through solder or oxide bonding techniques.

In the OPA device 1500/1500', sub-circuit chips may be thinned using wafer thinning techniques to be thin enough such that the entire system is such that the thickness dimension TH satisfies the expression 1 mm$<=$TH$<=$3 mm. These techniques are employed in stacked memory chips with wafers thinned to less than 20 μm thick and bonded to other wafers and connecting micro-TSVs are made between active layers that are 10 μm to 20 μm tall. The OPA device 1500/1500' may be constructed such that the width dimension W satisfies the expression 1 mm<=W<=10 mm. An OPA device having these dimensions TH and W is suitable for implant in an eye, such as shown at FIGS. 5-7.

In the OPA device 1500/1500', each sub-circuit system may be made with a different material technology and may be aligned and integrated such that they are on the same level as shown in the case of the optical source generation circuitry 1545 and the OPA 1550 being in a same layer in FIG. 16. Additionally, the OPA 1550 may comprise integrated subcomponents such as SOI chips and Liquid Crystal cavities acting as voltage controlled optical phase shifters.

In the OPA device 1500/1500', the control circuitry 1540 may contain wireless communication circuitry such that the integrated system could be programmed externally. In embodiments, once the image mapping to healthy retinal tissue is programmed, the device does not need any wireless communication to produce a retinal image in the healthy regions of the retina. The wireless communication antenna (s) for this system could be in the chips themselves (e.g., in the control circuitry 1540) or can be co-fabricated in the haptics as shown at elements 1525.

In embodiments, the power source 1535 comprises a rechargeable battery that can be wirelessly recharged through inductive coupling using the inductive coupling coils 1520 and an external charging coil, such as those illustrated in FIGS. 14A and 14B.

In embodiments, the OPA 1550 comprises an on-chip optical phased array that is capable of beam steering to project a visible light in a desired direction to create a projection of an image. On-chip optical phased arrays are understood by those of skill in the art, and any suitable fabrication may be used in implementations of the invention. For example, the optical phase shifters could use TiN micro heaters as actuators which would give KHz range responsivity, and are compact, but also have higher power consumption. They could also be PN-diode based charge injection phase shifters that use the carrier concentration near a PN interface to modulate optical index and therefore light (these have a responsivity in the MHz range, but they can be larger in size). The optical phase shifter could also be made of MOS actuators such that the charge concentration which modulates the optical index/phase is actuated by MOS cap carrier accumulation under an electrode (these can be larger in size, but are low power, and have responsivity in the GHz range). Further, the optical phase shifter could be fabricated with micro liquid crystal cavities, or through moving micro-mechanical systems (MEMs). The optical antennas of the phased array could be straight waveguide grating antennas, arc grating antennas, or different technologies in development such as hybrid plasmonic nano-antennas, which would be well-suited for rapidly controllable, 2D OPAs to maximize beam steering angle and optimizing quasi near-field beam formation on the retina nerve surface.

Still referring to FIGS. 15 and 16, the imaging system 1530 may comprise any suitable type of on-chip imaging technology, such as a charge-coupled device (CCD). The imaging system 1530 may also include specialized local lens structures to enhance functionality of imaging chip. In embodiments, the output of the imaging system 1530 is a time-dependent electronic signal to control circuitry 1540. In embodiments, the control circuitry 1540 takes input of a time-dependent video signal, and an essentially fixed, but wirelessly programmable, mapping stored in memory (for example, in on-chip RAM) that is used to control where each pixel will be mapped to the retina surface. In embodiments, this programmable mapping is determined after diagnostic mapping as described, for example, at FIG. 17. During a programming phase, a wireless signal for the mapping is received through the wireless communication antenna 1525 which may be in the haptics and spiral around the center chipset as shown depicted in cross-section in FIGS. 15 and 16.

In embodiments, the control circuitry 1540, once programmed with the desired mapping, controls the optical source generation circuitry 1545 with a time-dependent output that will control the phase shifters and optical source chips. In embodiments, the optical source generation circuitry 1545 can be located in a stack vertically separated from the OPA 1550 (e.g., as shown in FIG. 15) or can be in a same level as the OPA 1550 (e.g., as shown in FIG. 16). This may be done to maximize the coupling efficiency between the optical source and the waveguide chips, e.g., vertical beam input versus lateral beam input.

In embodiments, the optical source generation circuitry 1545 generates an output that is provided as an input to the OPA 1550, which may be an optical signal. In some embodiments, the optical signal in the visible wavelength range. In other embodiments, the optical signal is outside the visible wavelength range but is shifted to the visible wavelength range by the OPA 1550. In a particular example, the optical source generation circuitry 1545 provides a source of laser light for the OPA 1550. In this example, the optical source generation circuitry 1545 generates a laser beam source which is aligned and coupled into the OPA 1550 (e.g., either side-coupled or surface-coupled through grating waveguide couplers) from the optical source generation circuitry 1545 into the OPA 1550. The laser light coupled into the OPA 1550 is then routed using on-chip optical waveguides on the OPA 1550 to the various components of the OPA 1550 (e.g., phase shifters, optical antenna, etc.), where ultimately, it exits the OPA 1550 through an array of optical antennas which are targeting the image location points on the retina Still referring to FIGS. 15 and 16, in an example embodiment, the OPA 1550 comprises an on-chip OPA that includes a splitter that splits the incoming optic signal into a plurality of optic signals, which are fed to a plurality of waveguides that are configured to carry optical signals in the visible wavelength range. The OPA 1550 can comprise a plurality of phase shifters that are coupled to respective ones of the plurality of waveguides, wherein the phase shifters are configured to shift the phase of the optical signals travelling in the waveguides. The OPA 1550 can comprise a plurality of emitters optically coupled to the plurality of waveguides, wherein a respective emitter receives an optical signal from its connected waveguide and outputs that optical signal by projecting the optical signal outward from the OPA 1550 (e.g., toward the retina). As is understood in the art, the outputs of plural emitters are combined through constructive and/or destructive interference to form a beam that is projected in a desired direction outward from the optical phased array, where the direction of the beam is controlled using the amount of phase shift applied at each of the wave guides. In this manner, the OPA 1550 may be used to output a beam of visible light in a desired direction toward the retina, e.g., to project an image on a healthy area of the retina as defined in the mapping.

With continued reference to FIGS. 15 and 16, in embodiments the power source 1535 comprises an integrated battery component. Use of a battery is optional and provides the ability for the OPA device to operate for a time period without continuous inductive power coupling. In an alternative embodiment, the OPA device does not include a battery, and instead is powered continuously using inductive coupling. In the embodiments, one or more capacitors integrated into the chip assembly can be used to smooth the power supply from inductive charging coupling which may vary in strength versus time.

Still referring to FIGS. 15 and 16, in embodiments the functionalities of each of the sub-component chips may be implemented with fewer layers, e.g., using only one or two larger substrates (1 to 10 mm in diameter) with several smaller chips attached. FIGS. 15-16 show cross-sections of particular implementations, but other integration/lateral/vertical chip attachments and placements are also contemplated.

FIG. 17 shows a flowchart of an exemplary method in accordance with aspects of the invention. The method may be carried out using the any of the OPA devices 500/600/700. At step 1701, the implanted OPA device projects an image on a small spot on the retina. At step 1702, the person indicates (e.g., via verbal feedback) whether they can or cannot see the spot. At step 1703, the system records the indication (yes or no) and the settings of the OPA device (e.g., the phase shifter settings that control the direction of the beam projected from the OPA). At step 1704, the OPA device changes the settings to the change the direction of the projected beam to a different location on the retina. The method then returns to step 1701 to repeat the projecting (step 1701), receiving feedback (step 1702), and recording (step 1703). By following this method and marching through plural discrete directions of the beam, the system can be used to create the mapping of which directions of the beam point toward a healthy part of the retina and which directions of the beam point toward a damaged part of the retina. In embodiments, this scanning is performed initially using a coarse grid 1710 (e.g., as shown in FIG. 17B) and then using a smaller sized grid 1715 (e.g., as shown in FIG. 17C). In embodiments, the mapping determined using this method is programmed to the control circuitry 1540 of the OPA device, e.g., using the wireless communication antenna 1525 as described herein. In embodiments, after being programmed, the mapping is used by the control circuitry 1540 of the OPA device to control the OPA 1550 to form a beam in a desired direction onto a healthy area of the retina.

Figures 18A, 18B:
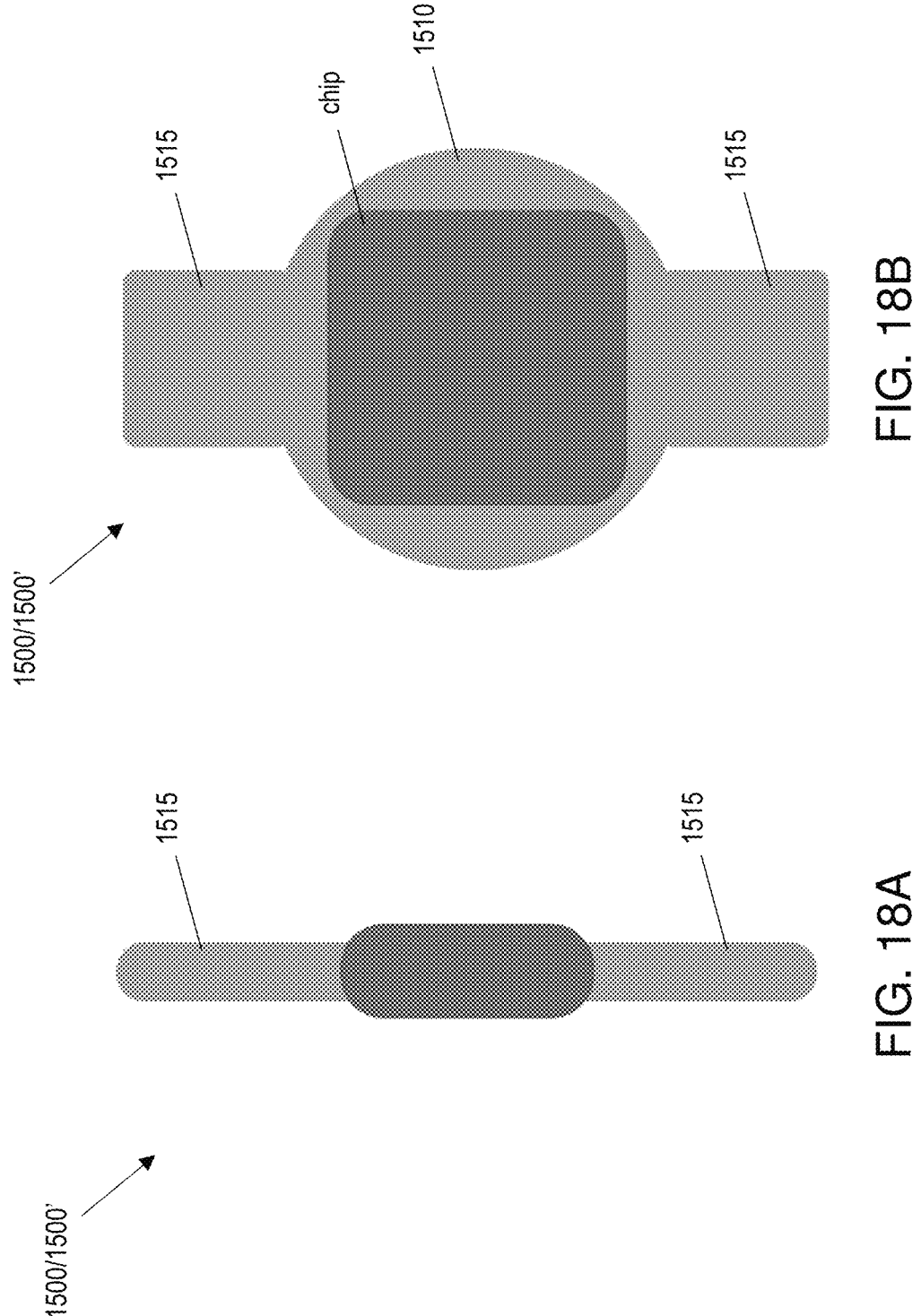
FIGS. 18A and 18B show a side view and a top view, respectively, of an OPA device in accordance with aspects of the invention.

FIGS. 18A and 18B show a side view and a top view, respectively, of the OPA device 1500/1500'. As shown in FIGS. 18A and 18B, the OPA device 1500/1500' includes a body comprising a center portion 1510 and haptics 1515. A chip (e.g., a stacked chip structure) containing the on-chip elements is disposed in the center portion 1510. The body may be composed of acrylic and/or silicone lens material, e.g., to form a single piece implantable lens replacement. The haptics 1515 allow for locating the OPA device 1500/1500' in the center of the capsular bar or ciliary sulcus.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

14

What is claimed is:

1. A device configured to be implanted in an eye, comprising:
   an imaging system that receives visible light incoming to the eye;
   optical source generating circuitry that generates an optical signal based on the light received by the imaging system;
   an optical phased array (OPA) that generates and projects an image onto a retina of the eye in which the device is implanted, the image being based on the optical signal generated by the optical source generating circuitry; and
   control circuitry that controls the OPA to project the image onto a determined area of the retina using beam steering that is controlled based on a stored mapping that maps the retina into functional areas and non-functional areas.

2. The device of claim 1, further comprising a rechargeable battery that is configured to power the imaging system, the control circuitry, the optical source generating circuitry, and the OPA.

3. The device of claim 2, wherein the rechargeable battery is configured to be recharged wirelessly from a charging system located outside the eye.

4. The device of claim 1, wherein the device is configured to be implanted in a capsular bag of the eye.

5. The device of claim 1, wherein the device is configured to be implanted in a ciliary sulcus of the eye.

6. The device of claim 1, wherein the device is configured to be implanted in a chamber of the eye anterior to the iris.

7. A method comprising implanting the device of claim 1 into the eye.

8. The device of claim 1, wherein:
   an imaging chip comprises the imaging system;
   a control chip comprises the control circuitry;
   an OPA chip comprises the OPA; and
   the imaging chip, the control chip, and the OPA chip are respective semiconductor chips that are arranged in a chip stack.

9. The device of claim 8, wherein:
   the imaging chip is at a first side of the chip stack;
   the OPA chip is at a second side of the chip stack opposite the first side of the chip stack;
   the control chip is between the imaging chip and the OPA chip in the chip stack; and
   the chip stack comprises one or more of a ball grid array, a controlled collapse chip connection, or through substrate vias.

10. A device configured to be implanted in an eye, comprising:
   an imaging system that receives visible light incoming to the eye;
   optical source generating circuitry that generates an optical signal based on the light received by the imaging system;
   an optical phased array (OPA) that generates and projects an image onto a retina of the eye in which the device is implanted, the image being based on the optical signal generated by the optical source generating circuitry; and
   control circuitry that causes the OPA to project the image onto a determined area of the retina,
   wherein the determined area of the retina is a healthy area of the retina, and
   the control circuitry determines the determined area of the retina using a stored mapping.

11. The device of claim 10, wherein the imaging system, the control circuitry, the optical source generating circuitry, and the OPA are arranged in a chip stack.

12. The device of claim 11, wherein:

the imaging system is at a first side of the chip stack; and the OPA is at a second side of the chip stack opposite the first side of the chip stack.

13. The device of claim 12, wherein:

the device comprises a body comprising a central portion and haptics extending outward from the central portion; and the chip stack is in the central portion.

14. The device of claim 10, further comprising a wireless communication antenna that is configured to receive wireless communication signals from outside the device.

15. The device of claim 14, wherein the control circuitry is configured to program the mapping based on the wireless communication signals.

16. A method of using a device configured to be implanted in an eye, the device comprising an imaging system that receives visible light incoming to the eye, optical source generating circuitry that generates an optical signal based on the light received by the imaging system, and an optical phased array (OPA) that generates and projects an image onto a retina of the eye in which the device is implanted, the image being based on the optical signal generated by the optical source generating circuitry, the method comprising:

causing the device to project a diagnostic image on different locations of the retina of the eye;

receiving patient feedback for each of the different locations;

creating a mapping of the retina of the eye based on the feedback; and programming the mapping into the device.

17. The method of claim 16, further comprising optimizing the mapping using artificial intelligence.

18. The method of claim 16, wherein the mapping maps the retina into functional areas and non-functional areas.

19. The method of claim 16, wherein the device is configured to control one or more elements of the OPA based on the mapping to project a beam onto a functional area of the retina to reduce or eliminate a scotoma caused by a non-functional area of the retina.

20. The method of claim 16, wherein:

the eye is in a patient from which the patient feedback is received; and the patient feedback indicates whether the patient can or cannot see the diagnostic image at respective ones of the different locations onto which the diagnostic image is projected.

* * * * *